(12) United States Patent
Geddes

(10) Patent No.: US 8,906,701 B2
(45) Date of Patent: Dec. 9, 2014

(54) SONICATION-ASSISTED METAL-ENHANCED FLUORESCENCE (SAMEF)-BASED BIOASSAYS

(75) Inventor: Chris D. Geddes, Bel-Air, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 802 days.

(21) Appl. No.: 13/063,501

(22) PCT Filed: Sep. 11, 2009

(86) PCT No.: PCT/US2009/056582
§ 371 (c)(1),
(2), (4) Date: May 5, 2011

(87) PCT Pub. No.: WO2010/030828
PCT Pub. Date: Mar. 18, 2010

(65) Prior Publication Data
US 2011/0207236 A1    Aug. 25, 2011

Related U.S. Application Data

(60) Provisional application No. 61/096,181, filed on Sep. 11, 2008.

(51) Int. Cl.
| G01N 33/553 | (2006.01) |
| C12Q 1/68 | (2006.01) |
| G01N 21/76 | (2006.01) |
| G01N 21/64 | (2006.01) |
| G01N 35/00 | (2006.01) |

(52) U.S. Cl.
CPC ............ G01N 21/76 (2013.01); C12Q 1/6832 (2013.01); G01N 2035/00554 (2013.01); G01N 21/648 (2013.01)
USPC ............ 436/525; 435/7.1; 435/7.92; 436/518

(58) Field of Classification Search
None
See application file for complete search history.

(56) References Cited

U.S. PATENT DOCUMENTS

| 5,017,009 A | 5/1991 | Schutt et al. |
| 5,449,918 A | 9/1995 | Krull et al. |
| 5,866,433 A | 2/1999 | Schalkhammer et al. |
| 7,095,502 B2 | 8/2006 | Lakowicz et al. |
| 7,253,452 B2 | 8/2007 | Steckel et al. |
| 7,348,182 B2 | 3/2008 | Martin et al. |
| 7,351,590 B2 | 4/2008 | Martin |
| 7,400,397 B2 | 7/2008 | Lakowicz et al. |
| 7,648,834 B2 | 1/2010 | Moore |
| 7,718,445 B2 | 5/2010 | Martin |
| 7,718,804 B2 | 5/2010 | Geddes et al. |
| 7,939,333 B2 | 5/2011 | Geddes et al. |
| 8,008,067 B2 | 8/2011 | Geddes et al. |
| 8,034,633 B2 | 10/2011 | Geddes |
| 8,075,956 B2 | 12/2011 | Geddes et al. |
| 2003/0022246 A1 | 1/2003 | Ogura et al. |
| 2003/0228682 A1 | 12/2003 | Lakowicz et al. |
| 2005/0053974 A1 | 3/2005 | Lakowicz et al. |
| 2005/0123563 A1 | 6/2005 | Doranz et al. |
| 2006/0147927 A1 | 7/2006 | Geddes et al. |
| 2007/0269826 A1 | 11/2007 | Geddes et al. |
| 2008/0194044 A1* | 8/2008 | Faris et al. ............. 436/537 |
| 2008/0215122 A1 | 9/2008 | Geddes et al. |
| 2009/0022766 A1 | 1/2009 | Geddes et al. |
| 2009/0325199 A1 | 12/2009 | Geddes et al. |
| 2010/0062545 A1 | 3/2010 | Geddes et al. |
| 2010/0209937 A1 | 8/2010 | Geddes et al. |
| 2010/0297016 A1 | 11/2010 | Geddes et al. |
| 2011/0020946 A1 | 1/2011 | Geddes |
| 2011/0136154 A1 | 6/2011 | Geddes |

FOREIGN PATENT DOCUMENTS

| GB | EP 0137678 | * 4/1985 | ............ G01N 33/53 |
| WO | WO89/09408 | 10/1989 | |
| WO | WO2004/024191 | 3/2004 | |
| WO | 2006-027738 | 3/2006 | |
| WO | WO2006/074130 | 7/2006 | |
| WO | 2006-137945 | 12/2006 | |
| WO | 2006-138698 | 12/2006 | |

OTHER PUBLICATIONS

Asian et al., Rapid Depositon of Triangular Silver Nanoparticles on Planar Surfaces: Application to Metal-Enhanced Fluorescence, J. Phys. Chem. B 2005, 109, pp. 6247-6251.*

Pompa et al., Metal-enhanced fluorescence of colloidal nanocrystals with nanoscale conrol, Nature Nanotechnology, col. 1, Nov. 2006, pp. 126-130.*

Matveeva et al., Myoglobin immunoassay based on metal particle-enhanced fluorescence, Journal of Immunological Methods 302, 2005, pp. 26-35.*

Aslan, K.; Geddes, C. D., Microwave-accelerated metal-enhanced fluorescence: Platform technology for ultrafast and ultrabright assays, *Analytical Chemistry* 2005, 77, 8057-8067.

Aslan, K.; Gryczynski, I.; Malicka, J.; Matveeva, E.; Lakowicz, J. R.; Geddes, C. D, Metal-enhanced fluorescence: an emerging tool in biotechnology, *Current Opinion in Biotechnology* 2005, 16, 55-62.

(Continued)

*Primary Examiner* — Gary W Counts
(74) *Attorney, Agent, or Firm* — Marianne Fuierer; Moore & Van Allen, PLLC

(57) ABSTRACT

The present invention provides for sonication-assisted metal-enhanced fluorescence, luminescence, and/or chemiluminescence assay systems using low-intensity ultrasound waves to significantly reduce the assay time by increasing the kinetic movement of molecules within the system.

6 Claims, 20 Drawing Sheets

(56) References Cited

OTHER PUBLICATIONS

Aslan, K.; Lakowicz, J. R.; Szmacinski, H.; Geddes, C. D., Enhanced ratiometric pH sensing using SNAFL-2 on silver island films: Metal-enhanced fluorescence sensing, *Journal of Fluorescence* 2005, 15, 37-40.

Aslan, K., Leonenko, Z., Lakowicz. J.R., Geddes, C.D., Annealed silver-island films for applications in metal-enhanced fluorescence: Interpretation in terms of radiating plasmons, J. Fluoresc. 2005, 15, 643-654.

Aslan, K.; Holley, P.; Geddes, C. D., Microwave-Accelerated Metal-Enhanced Fluorescence (MAMEF) with silver colloids in 96-well plates: Application to ultra fast and sensitive immunoassays, High Throughput Screening and drug discovery, *Journal of Immunological Methods* 2006, 312, 137-147.

Aslan, K.; Zhang, Y.; Hibbs, S.; Baillie, L.; Previte, M. J.; Geddes, C. D., Microwave-accelerated metal-enhanced fluorescence: application to detection of genomic and exosporium anthrax DNA in < 30 seconds, *Analyst* 2007, 132, 1130-1138.

Aslan, K.; Geddes, C. D., Microwave-accelerated Metal-enhanced Fluorescence (MAMEF): Application to ultra fast and sensitive clinical assays, *Journal of Fluorescence* 2006, 16, 3-8.

Collings, F. B.; Vaidya, V. S. : Novel technologies for the discovery and quantitation of biomarkers of toxicity, *Toxicology* 2008, 245, 167-174.

Enander, K.; Choulier, L.; Olsson, A. L.; Yushchenko, D. A.; Kanmert, D.; Klymchenko, A. S.; Demchenko, A. P.; Mely, Y.; Altschuh, D., A peptide-based, ratiometric biosensor construct for direct fluorescence detection of a protein analyte, *Bioconjug Chem* 2008.

Geddes, C. D.; Lakowicz, J. R., Metal-enhanced fluorescence, *Journal of Fluorescence* 2002, 12, 121-129.

Gould, R. K.; Coakley, W. T.; Grundy, M. A., Upper Sound Pressure Limits on Particle Concentration in Fields of Ultrasonic Standing-Wave at Megahertz Frequencies, *Ultrasonics* 1992, 30, 239-244.

Green, N.M.; Geddes, C.D.., Avidin, Protein Chem. 1975, 29, 85-133.

Lalvani, A.; Meroni, P. L.; Millington, K. A.; Modolo, M. L.; Plebani, M.; Tincani, A.; Villalta, D.; Doria, A.; Ghirardello, A., Recent advances in diagnostic technology: applications in autoimmune and infectious diseases, *Clin Exp Rheumatol* 2008, 26, S62-66.

Lofas, S.; Malmqvist, M.; Ronnberg, I.; Stenberg, E.; Liedberg, B.; Lundstrom, I., Bioanalysis With Surface-Plasmon Resonance, *Sensors and Actuators B—Chemical* 1991, 5, 79-84.

Matveeva, E.; Gryczynski, Z.; Gryczynski, I.; Malicka, J.; Lakowicz, J. R., Myoglobin immunoassay utilizing directional surface plasmon-coupled emission, *Analytical Chemistry* 2004, 76, 6287-6292.

Matveeva, E.; Malicka, J.; Gryczynski, I.; Gryczynski, Z.; Lakowicz, J. R., Multi-wavelength immunoassays using surface plasmon-coupled emission *Biochem Biophys Res Commun* 2004, 313, 721-726.

Neppiras, E. A., Acoustic Cavitation, *Phys. Rep.* 1980, 61, 159-251.

Schultz, E.; Galland, R.; Du Bouetiez, D.; Flahaut, T.; Planat-Chretien, A.; Lesbre, F.; Hoang, A.; Volland, H.; Perraut, F., A novel fluorescence-based array biosensor: Principle and application to DNA hybridization assays, *Biosens Bioelectron* 2008, 23, 987-994.

Suslick, K. S., Sonochemistry, *Science* 1990, 247, 1439-1445.

Suslick, K. S.; Flannigan, D. J., Inside a collapsing bubble: Sonoluminescence and the conditions during cavitation, *Annu Rev Phys Chem* 2008, 59, 659-683.

G. Bauer, F. Pittner and Th. Schalkhammer, Metal Nano-Cluster Biosensors, Mikrochim. Acta 131, 107-114 (1999).

Th. Schalkhammer, Metal Nano Clusters as Transducers for Bioaffinity Interactions, Monatschefte für Chemie 129, 1067-1092 (1998).

Taipa, M. A., Immunoassays: Biological tools for high throughput screening and characterisation of combinatorial libraries, *Comb Chem High Throughput Screen* 2008, 11, 325-335.

Thornycroft, L. H.; Barnaby, S. W., Torpedo-Boat Destroyers, *Min. Proc. Inst. Chem. Eng*, 1895, 122 51-69.

\* cited by examiner

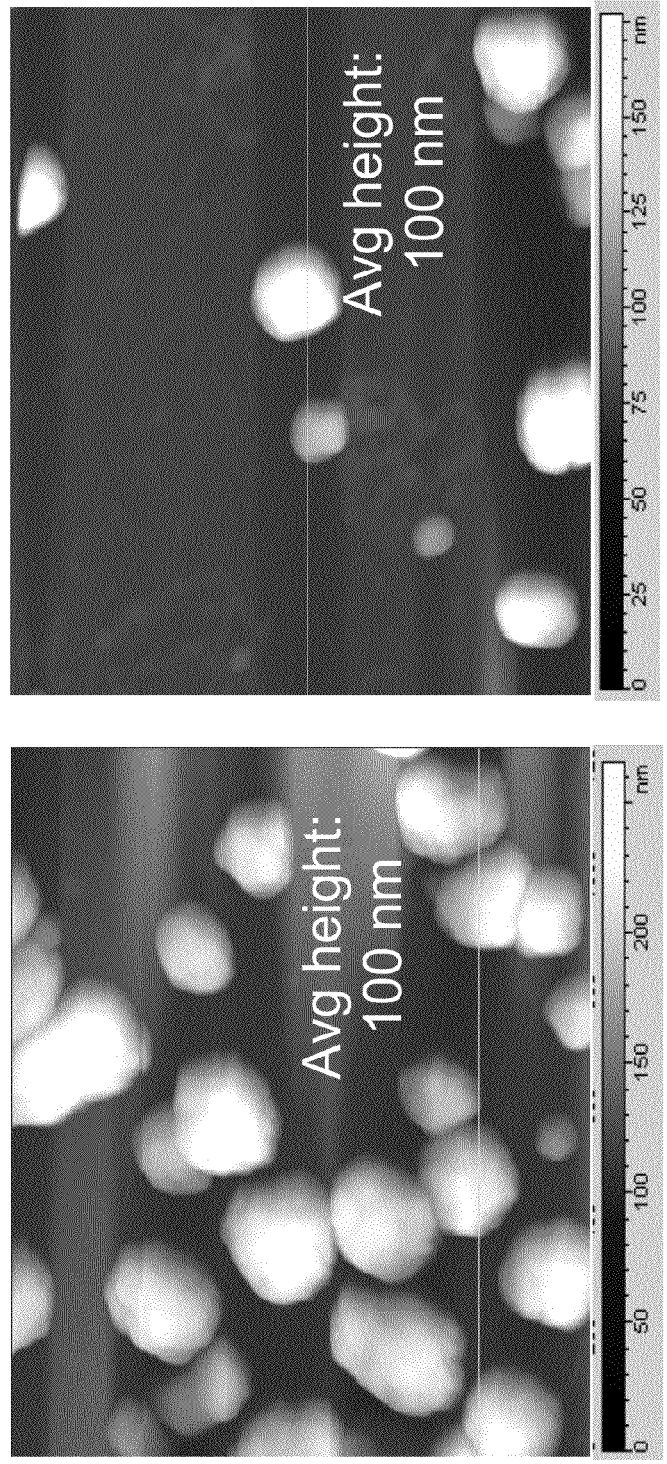
Figures 1B and C

SONICATION-ASSISTED METAL-ENHANCED FLUORESCENCE (SAMEF)-BASED BIOASSAYS

CROSS-REFERENCE TO RELATED APPLICATIONS

This application is filed under the provisions of 35 U.S.C. §371 and claims the priority of International Patent Application No. PCT/US2009/056582 filed on Sep. 11, 2009, which in turn claims priority of U.S. Provisional Application No. 61/096,181 filed on Sep. 11, 2008, the contents of which are hereby incorporated by reference herein for all purposes.

BACKGROUND OF THE INVENTION

1. Technical Field

The present invention is directed to a metal-enhanced detection system and method for increasing sensitivity and rapidity of the detection system, and more particularly, using sonication in combination with metallic enhanced, fluorescence or chemiluminescence detection assays to increase the speed and sensitivity of the detection system.

2. Background of Related Art

The identification and quantification of proteins and other biomolecules using bioassays are of great importance in biomedical and biochemical applications.[1-3] Fluorescence is the dominant technology in most of these applications, where a biomolecule of interest is detected by fluorescence emission from its fluorophore labeled binding partner.[4, 5] Fluorescence-based bioassays those carried out on planar surfaces generally lack sensitivity and require expensive optical instruments.[6, 7] In addition, the biorecognition events in these assays are inherently slow (several minutes to hours).[6, 7] The sensitivity of the fluorescence-based assays can be improved, without the use of high-end optical instruments, by incorporating plasmon resonant particles (PSPs) into these assays.[8, 9] The improved sensitivity is made possible by the increase in fluorescence signatures and decreased lifetimes of fluorophores placed in close proximity to PSPs, described by a phenomenon called Metal-Enhanced Fluorescence (MEF).[8, 10] In MEF-based bioassays, PSPs (generally silver nanoparticles) are deposited onto the planar surface and the bioassay is constructed on the PSPs.[8] Since the size of most biomolecules are smaller than PSPs (20-100 nm), fluorophores are positioned within a distance where their emission is increased due to their interactions with the surface plasmons of PSPs.[10]

Although the sensitivity of fluorescence-based bioassays is addressed by MEF, the speed of the bioassays remains a huge challenge to overcome. In this regard, a new technique, called Microwave-Accelerated Metal-Enhanced Fluorescence (MAMEF)[11] that amalgamates low power microwave heating and MEF was shown to decrease the bioassay completion times to less than 1 min. In MAMEF, low power heating of the assay components creates a temperature gradient between the bulk (target biomolecules and fluorescent probes are present) and the silver nanoparticles at the assay surface (capture probe is present), which drives the target biomolecules and fluorescent probes towards the surface and the bioassay is constructed.[11] The microwave heating step can be carried out separately for each assay component or in one step for a 3-piece DNA hybridization assay.[12] However, several factors affect the efficiency of the MAMEF technique: 1) assay surfaces have to be modified to remove excess heating (especially in assays run with small volume of liquid),[11] 2) the heating of large assay platforms with multiple sharp corners[13] (e.g., High Throughput Screening Wells) require longer heating times that subsequently lead to the evaporation of sample.

In surface plasmon-coupled chemiluminescence (SPCC), where the luminescence from chemically induced electronic excited states couples to surface plasmons in metalized particles or surfaces, the kinetics of the systems relies on chemically induced electronically excited states that occur without an external excitation source. However, in chemiluminescence systems, detection is limited by the quantum efficiency of the chemiluminescence reaction or probe, and the time before depletion of the reactants. Thus, it would be beneficial to increase the movement of the reactants to increase the speed of the chemiluminescence reaction.

In this regard, there is still a need for a more generic technique applicable to all commercially available assay platforms without the sacrifice of samples.

SUMMARY OF THE INVENTION

The present invention provides for sonication-assisted metal-enhanced fluorescence, luminescence, and/or chemiluminescence assay systems using low-intensity ultrasound waves to significantly reduce the assay time by increasing the kinetic movement of molecules within the system.

In one aspect the present invention relates to an assay detection method comprising:
  providing a conductive metallic material; wherein the metallic material is shaped as a just-continuous film or particles that include nanostructures, island or colloids;
  introducing at least one molecule and/or fluorophore for disposing near the conductive metallic material, wherein the molecule and/or fluorophore is capable of emitting light and enhanced by proximity to the metallic material ranging from about 5 nm to 50 nm;
  applying ultrasonic energy to cause an increase in the kinetics of chemical reactions involving the molecule; and
  measuring the emitted light from the system.

The method described above may be used in multiple detecting systems, including but not limited to, immunoassays, hybridization assays, resonance energy transfer assays, polarization/anisotropy based assays, chemiluminescence based assays, luminescence based assays, and enzyme-linked immunosorbent assays.

In another aspect, the present invention provides for a detection system comprising:
  a conductive metallic material positioned within a container, wherein the metallic material is shaped as a just-continuous film, particles, nanostructures, island or colloids;
  at least one biomolecule for disposing near the conductive metallic material, wherein the biomolecule is capable of emitting light when excited by an electromagnetic source and enhanced by a predetermined proximity to the metallic material;
  a source of sonic energy to cause an increase movement of at least the biomolecules in the fluids near the metallic surfaces thereby increasing the kinetics of a chemical reactions involving the biomolecule; and
  a measuring device to measure the emitted light from the system.

In the present embodiment, the biomolecule comprises either an extrinsic or intrinsic fluorescing component that has the ability to fluoresce when contacted with radiation in the range from UV to IR. Preferably, the fluorescing component is a molecule that does not interfere with the chemical reaction of the biomolecule.

In yet another aspect, the present invention relates to a method of decreasing detection time of a metal-enhanced fluorescence assay used for detection of a target molecule, the method comprising:
- applying a multiplicity of metallic particles to a substrate surface used in the assay system;
- connecting capture molecules to the metallic particles, wherein the capture molecules have binding affinity for the target molecules;
- introducing a solution suspected of including the target molecules;
- applying sonic energy to the assay system for a time period sufficient to increase movement of molecules towards the metallic particles thereby binding with capture molecules;
- introducing fluorescence detector molecules having affinity for the target molecules, wherein the fluorescence detector molecules can be added before, during or after the application of sonic energy;
- applying electromagnetic energy at a frequency to excite the fluorescence molecules; and
- measuring any fluorescence signal.

In a still further aspect the present invention relates to a method of metal-enhanced fluorescence sensing, comprising:
- applying a conductive metallic material to a surface substrate used in a detection system, wherein the surface includes glass, quartz, or a polymeric material;
- introducing a solution containing at least one molecule for disposing near the conductive metallic surface, wherein the molecule is capable of fluorescing or in the alternative capable of binding with a fluorescing molecule;
- applying sonic energy in a range from 20 to 200 kHz to cause an increase in movement of the molecule is the solution thereby increasing the kinetics of any chemical reactions occurring within the detection system;
- exciting the molecule with an electromagnetic source to cause fluorescing; and
- measuring the fluorescence emission within the system.

In all embodiments, the metallic material may comprise silver, gold, copper, zinc, nickel, iron, palladium, aluminum, platinum or any metal exhibiting plasmonic emission. The metallic material may take the form of metallic islands, nanostructures, colloids, porous matrix, metallic particles impregnated within a glass or polymeric surface and/or a metallic surface in a patterned shape.

The patterned shape includes metallic containing shapes having at least one apex wherein the shape includes but is not limited to a triangle, square, rectangle, trapezoid, polygon, elliptical, oblong or combinations thereof. Further, emissions and reactivity can be enhanced by placement of metallic structures having a shape with an apex area and positioning such apex areas adjacent to each other and creating a reactive zone therebetween. The reactive zone therebetween is prepared for placement of the immobilized capture molecule complementary to a target molecule. The metallic structures when fabricated into geometric shapes comprising an apex area for forming a reactive zone can be positioned on assay system with multiple wells wherein the reactive zone includes the wells and exposure to low-intensity ultrasound increases the reactivity and shortens the completion time of the detection assay.

The surface substrate may be fabricated of a polymeric material, glass, paper, nitrocellulose, combinations thereof or any material that provides sufficient stability for placement of the metallic structures.

In yet another aspect, the present invention provides a method for detecting a targeted pathogen in a sample, the method comprising:
- providing a system comprising:
  - an immobilized metallic material positioned on a surface substrate, wherein the immobilized metallic material has attached thereto an immobilized capture DNA sequence probe complementary to a known DNA sequence of the target pathogen; and
  - a free capture DNA sequence probe complementary to a known DNA sequence of the target pathogen, wherein the free capture DNA sequence probe has attached thereto a fluorophore;
- contacting the sample with the immobilized capture DNA sequence probe, wherein the DNA sequence of the target pathogen binds to the immobilized capture DNA sequence probe;
- contacting the bound DNA sequence of the target pathogen with the free capture DNA sequence probe, wherein binding of the free capture DNA sequence probe to the DNA sequence of the target pathogen causes the fluorophore to be positioned a sufficient distance from the immobilized metallic material to enhance fluorescence emission;
- applying to the system ultrasound energy in an amount sufficient to increase movement of any DNA molecule of the target pathogen to the immobilized probe to enhance binding of the free capture DNA sequence probe to the DNA sequence of the target pathogen thereby causing increased speed of the reactions; and
- irradiating the system with electromagnetic energy in a range from UV to IR to increase fluorescence emission by the fluorophore positioned a predetermined distance from the metallic material, wherein the irradiating can be conducted before, during or after the applying of ultrasound energy.

The biomolecule that is capable of fluorescing and/or upon excitation by electromagnetic energy emits light includes, but is not limited to fluorophores, chromophores, or lumophores. The compound capable of fluorescing may be an intrinsic fluorophore or a compound attached to an extrinsic fluorophore.

In a further aspect, the present invention relates to bioassay systems comprising metallic surfaces for the enhancement of effects of chemiluminescence based reactions positioned near the metallic surfaces, wherein metallic surface plasmons are excited by a chemically induced electronically excited state of a chemiluminescent species and radiation emitted therefrom providing an enhanced signal. The surface plasmon-coupled chemiluminescence signal may include unpolarized, p-polarized and/or s-polarized signals.

In a still further aspect, the present invention relates to an assay using High Throughput Screening (HTS), the method comprising:
- providing a well plate used in HTS systems comprising a multiplicity of wells;
- introducing metallic nanostructures into the wells,
- introducing at least one biomolecule for disposing near the metallic nanostructures, wherein the biomolecule is capable of emitting light through excitation with electromagnetic energy or a chemical reaction and enhanced by a predetermined proximity to the metallic nano structures;
- applying sonic energy in a range to cause an increase in movement within the well thereby increasing the kinetics of chemical reactions involving the biomolecule and/or increasing speed of detection time; and measuring the emitted light from the system.

A further aspect of the present invention, relates to a kit for detecting a target molecule in a sample, the kit comprising a container comprising a layer of immobilized metal particles deposited on a substrate fabricated of a polymeric or quartz material, wherein an immobilized probe is connected to the metal particles and wherein the immobilized probe has an affinity for the target molecule;

a fluorophore having an affinity for the target molecule, wherein the binding of the target molecule to both the immobilized probe and fluorophore causes the fluorophore to be positioned a sufficient distance from the immobilized metal particles to enhance fluorescence emission; and a source of ultrasonic energy to increase movement in the system and a source of energy to excite the fluorophore.

In yet another aspect, the present invention relates to a method of metal-enhanced chemiluminescence sensing, comprising:

applying a metallic material to a surface used in a detection system; introducing a solution containing at least one biomolecule for disposing near the metallic surface, wherein the biomolecule comprises a chemiluminescent label;

triggering the chemiluminescent label to induce a chemically electronically excited state thereby generating metallic surface plasmons and applying sonic energy to the detection system before or during the triggering of the chemiluminescent label; and measuring the chemiluminescence signal.

In a still further aspect, the present invention provides a method for detecting a targeted pathogen in a sample, the method comprising:

providing a system comprising:

a metallic surface, wherein the metallic surface is connected to an immobilized capture nucleic acid sequence probe complementary to a known nucleic acid sequence of the target pathogen; and a free capture nucleic acid sequence probe complementary to the known nucleic acid sequence of the target pathogen, wherein the free capture nucleic acid sequence probe has attached thereto a chemiluminescent label;

contacting the sample with the immobilized capture nucleic acid sequence probe, wherein the nucleic acid sequence of the target pathogen binds to the immobilized capture nucleic acid sequence probe;

applying sonic energy to the system in an amount to increase movement of nucleic acid within the system;

contacting the bound nucleic acid sequence of the target pathogen with the free capture nucleic acid sequence probe for binding therewith;

introducing a trigger component to chemically react with the chemiluminescent label;

measuring the chemiluminescence signal intensity, wherein the signal is enhanced relative to system that does not include metallic surfaces.

In another aspect, the present invention relates to a system for measuring fluorescence or chemiluminescence signal, the system comprising:

a multiplicity of metalized particles positioned on a surface substrate;

a connector molecule attached to the metallized particles or near the metallized particles for binding or capture of a desired molecule in a testing sample;

a detector molecule having an affinity for the desired molecule, wherein the detector molecule comprises a fluorescence or chemiluminescence label;

a triggering component that chemically reacts with the chemiluminescence label to generate a chemically induced electronically exited state or an electromagnetic source to excite the fluorescence label;

a source of sonic energy; and a measuring device to measure surface plasmon coupled emissions.

Other aspects and advantages of the invention will be more fully apparent from the ensuing disclosure and appended claims.

DETAILED DESCRIPTION OF THE INVENTION

Figure 1A:
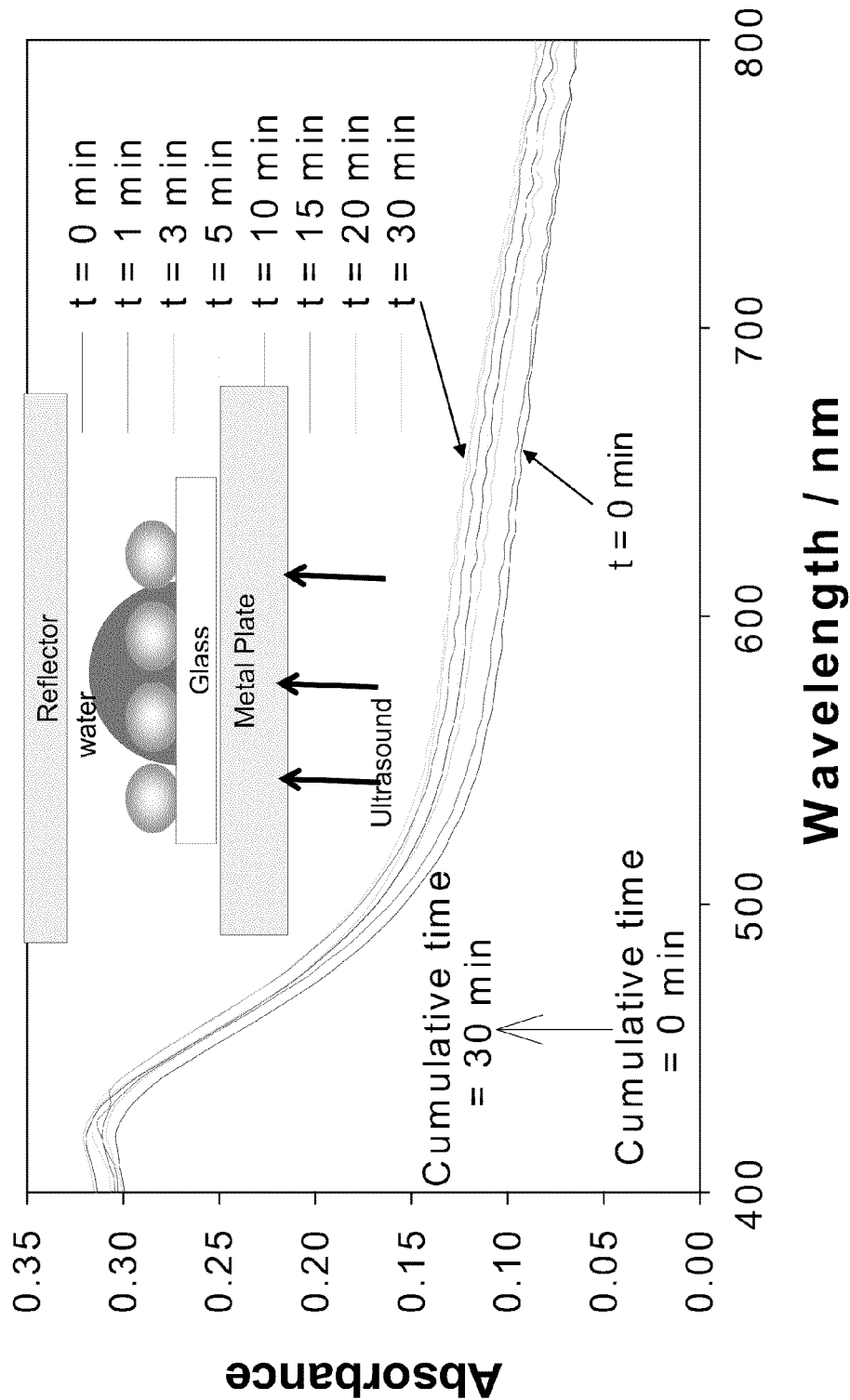
FIG. 1 (A) Absorption spectrum of Silver Island Films (SIFs) as a function of sonication time, the same sample was sonicated for a total of 30 minutes (500 microliter of deionized water was placed on top of the samples), Atomic Force Microscope images of SIFs (B) before and (C) after 1 min sonication. The reflector plate is located 2 cm from the surface of the glass.

The present invention relates to systems and methods for increasing and detecting the fluorescence of fluorescent, non-fluorescent compounds and light emitted from chemiluminescence reactions, by using low-intensity ultrasound to increase the kinetics of the system thereby increasing chemical or binding reactions to increase speed of detection system.

Since the first observation of cavitation effects created by ultrasound in 1895,[14] ultrasound has found many applications in chemical and physical processes, most notably, in speeding up chemical reactions (i.e., sonochemistry).[15] Cavitation effects, which are referred to rapid formation and implosion of small bubbles in a liquid, are typically observed for ultrasound frequencies lower than 1 MHz.[16] The implosion of bubbles (symmetric cavitation) result in hot spots in liquids and the temperature inside the bubble can reach in excess of 5000 K, which is subsequently quenched by surrounding water molecules at a rate of $10^{10}$K/sec.[17] When the bubbles collapse near a solid surface which is several orders of magnitude larger than the bubble, symmetric cavitation is hindered and the collapse of bubbles occurs asymmetrically.[18] Subsequently, this results in the formation of microjets of liquid perpendicular to the surfaces, which are estimated to reach speed of 100 m/s.[18] The formation and collapse of the microjets of liquid lead to stirring of liquid in the bulk in addition to their well-known cleaning effect.

The present invention relates to a new technique, called SAMEF, based on the combination of low-intensity ultrasound and MEF. The use of low-intensity ultrasound resulted in the significant reduction of the bioassay time (1 min) as compared to those assays run at room temperature without sonication (30 min). In addition, the MEF component afforded the increase in bioassay sensitivity through enhanced fluorescence signatures.

"Fluorophore or fluorescence molecule," as used herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phosphatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Also included are novel quaternary nitrogen heterocyclic boronic acid-containing compounds including:

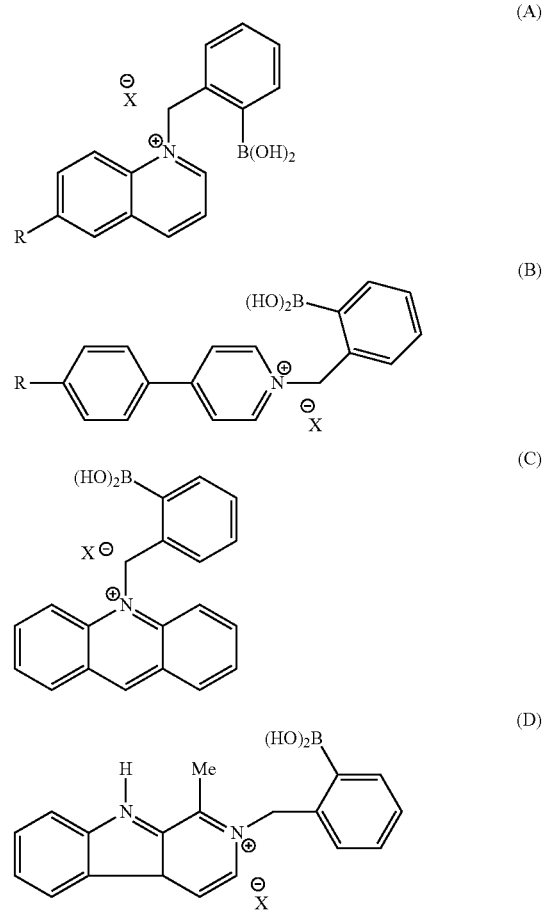

-continued

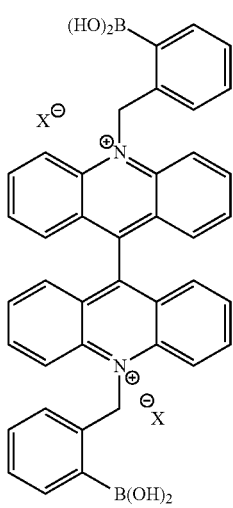

(E)

and

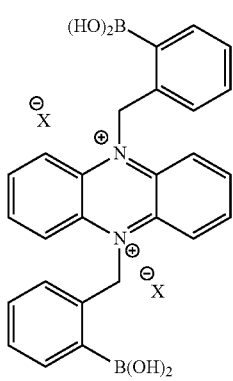

(F)

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups.

The term "biomolecule" means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies and phycobiliproptein.

Embodiments of the present invention are also applicable to chemiluminescence labels or moieties which participate in light-producing reactions in the presence of a triggering agent or cofactor. In the present application, for purposes of example and without limitation, a preferred embodiment will be discussed in terms of chemiluminescence labels and triggering agent. The label affixed to the detector molecule will be referred to as the "label" or "label agent". For purposes herein, "triggering agent or cofactor" is broadly used to describe any chemical species, other than the chemiluminescence labels which participates in a reaction and which produces a detectable response. Chemiluminescence labels and triggering agents produce a light response.

Examples of suitable chemiluminescence labels include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, an Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen.

Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

Techniques for attaching antibodies or antigens to solid substrates are also well known in the art. For example, antibodies may be coupled covalently using glutaraldehyde to a silane derivative of borosilicate glass.

Although chemiluminescence detection has been successfully implemented, the sensitivity and specificity of these reactions require further improvements to facilitate early diagnosis of the prevalence of disease. In addition, most protein detection methodologies, most notably western blotting, are still not reliable methods for accurate quantification of low protein concentrations without investing in high-sensitivity detection schemes. Protein detection methodologies are also limited by antigen-antibody recognition steps that are generally kinetically very slow and require long incubation times; e.g., western blots require processing times in excess of 4 h. Thus, both the rapidity and sensitivity of small-molecule assays are still critical issues to be addressed to improve assay detection. As such the use of low intensity ultrasound will increase the rapidity of the assay.

There are many important assays that can directly benefit from enhanced signal intensities and quicker kinetics. For example, myoglobin concentrations for heart attack patients, patients of toxic shock and pancreatitis. All of these assays are widely used in hospitals emergency rooms with assay times of greater than 30 minutes. Thus, the present invention can be used for points-of-care clinical assessment in emergency rooms.

The present invention is achieved by using any device capable of generating and transmitting acoustic energy through any medium to transit ultrasonic atomizing energy. The ultrasonic emitting device can be placed in either the interior of a vessel or positioned adjacent thereto for transmitting energy into the vaporization vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to $(R_1:R_2)$. Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

The assay systems of the present invention may further comprise a light or laser source for directing an energy beam on any included fluorophore to provide excitation energy. The laser beam may be positioned adjacent to the system for directing the beam at the molecular components. The laser may be any device capable of focusing an energy beam at a particular point on the solid or liquid source material for excitation and the laser may transmit RF, infrared, microwave to UV energy.

Any source, known to one skilled in the art may be used, such as a laser that emits light, wherein light is used in its broad sense, meaning electromagnetic radiation which propagates through space and includes not only visible light, but also infrared, ultraviolet radiation and or acoustic energy. Thus, a single instrument placed above the surface of the assay can be used to generate the acoustic energy and energy to excite fluorescing molecules or a chemiluminescence reaction. The light or sound waves can be emitted from a fiber continuously or intermittently, as desired, to increase the speed of chemical reactions within the assay system.

The present invention provides enhanced emissions using metallized islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 50 nm apart. In the continuous metallic film case, the fluorophore emissions could be detected in the analyte solution up to 500 nm away from the surface of the metal. In the case where the metallic coating is formed by islands, the enhanced fluorophore emissions could be detected in the solution up to 200 nm away from the surface of the metal.

In one embodiment the present invention provides for metallic material and a biomolecule capable of fluorescing, wherein the metallic material and the biomolecule are separated by at least one film spacer layer. The thickness of said film may be chosen so as to enhance the fluorescence of the biomolecule due to the distance of the biomolecule from the metallic material. The film spacer layer may be one or multiple layers of a polymer film, a layer formed from a fatty acid or a layer formed from an oxide. In a preferable embodiment, the film spacer layers and the metallic material are chemically inert and do not bind to the biomolecules to be detected or to intermediates that are bound to the compounds to be detected, for example covalently bound. The layer formed from a fatty acid may be formed by a Langmuir-Blodgett technique. The film spacer layer may be a spin coated polymer film. The oxide layer may be formed from a deposition technique, such as vapor deposition.

Further, the metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently.

Increase in Radiative Decay Rate

It is known that a nearby metal can increase the intrinsic decay rate of a fluorophore, that is, to modify the rate at which the fluorophore emits photons. In fluorescence, the spectral observables are governed by the magnitude of $\lambda$, the radiative rate, relative to the sum of the non-radiative decay rates, $k_{nr}$ such as internal conversion and quenching.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The ability to increase the radiative decay rate suggests that any chromophore, even non-fluorescent species such as bilirubin, fullerenes, metal-ligand complexes or porphyrins could display usefully high quantum yields when appropriately placed near a metal surface. The effects of metal surface-fluorophore interactions are highly dependent upon the distance between the metal surface and the species, and the nature of the metal surface.

The emission enhancement may be observed at distances according to the type of fluorophore to be detected and the type of metal. For example, emission enhancement may be observed when a fluorophore distances about 4 nm to about 200 nm to metal surfaces. Preferable distances are about 5 nm to about 50 nm, and more preferably, 10 nm to about 30 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Different surface enhanced fluorescence effects are expected for mirrors, sub-wavelength or semi-transparent metal surfaces, silver island films or metal colloids. More dramatic effects are typically observed for islands and colloids as compared to continuous metallic surfaces. The silver islands had the remarkable effect of increasing the intensity 5-fold while decreasing the lifetime 100-fold. Such an effect can only be explained by an increase in the radiative decay rate, Fluorescence or chemiluminescence signals can be detected using devices including, but not limited to, a spectrofluorometer having a light source and detector. Light sources can include arc lamps and lasers. Detectors can include photomultiplier tubes. Additionally, it is advantageous for the device to have a monochromator so that specific wavelengths of light may be used to excite a molecule or to detect emissions at a specific wavelength. When a sample containing a fluorophore is placed in the spectrofluorometer and exposed to an amount of exciting radiation, the fluorophore emits radiation that is detected by a photomultiplier tube. The fluorescence intensity of a biomolecule can be increased in response to an amount of exciting radiation when the distance between the metal particle and the biomolecule is from about 4 nm to about 200 nm. Preferable distances are about 5 nm to about 50 nm, and more preferably, 10 nm to about 30 nm. Alternatively, the fluorescence intensity of the biomolecule can be reduced when the distance between the biomolecule and the metal particle is less than about 40 Å due to quenching.

The present invention provides a method for increasing the fluorescence intensity of a fluorescently labeled biomolecule including the steps of labeling a biomolecule with a fluorophore, positioning the labeled biomolecule at a distance apart from a metallic particle such that in response to an amount of exciting radiation, the fluorophore emits radiation.

In applications of MEF, it was found that the enhanced fluorescence signals (Quantum yields—Qm) of fluorophores in close proximity (<10 nm) to metallic nanostructures could be well described by the following equations:

$$Q_m = (\Gamma + \Gamma_m)/(\Gamma + \Gamma_m + k_{nr}) \qquad (1)$$

where $\Gamma$ is the unmodified radiative decay rate, $\Gamma_m$ is the metal-modified radiative decay rate and $k_{nr}$ are the non-radiative rates. Similarly, the metal-modified lifetime, $\tau m$, of a fluorophore is decreased by an increased radiative decay rate:

$$\tau_m = 1/(\Gamma + \Gamma_m + k_{nr}) \qquad (2)$$

These equations have resulted in most unusual predictions for fluorophore-metal combinations, and it is these predictions and observations that are currently finding profound implications and applications in fluorescence based nanotechnology. Given that fluorescence has become the dominant tool in biotechnology today, then metal-enhanced and plasmon coupled fluorescence promises to change the way fluorescence is viewed. From equations 1 and 2, it can be seen that as the value of $\Gamma m$ increases, the quantum yield Qm increases, while the lifetime, $\tau m$, decreases. This is contrary to most observations in fluorescence where the free-space quantum yield, $Q_0$, and lifetime, $\tau_0$, usually change in unison as described by the well known equations:

$$Q_0 = \Gamma/(\Gamma + k_{nr}) \quad (3)$$

$$\tau_0 = 1/(\Gamma + k_{nr}) \quad (4)$$

In addition, one major criterion for choosing fluorophores in current immunoassays has been a high quantum yield. This can lead to a high background from either unlabelled fluorophores or a high fluorescence background from non-specific assay absorption. However, metal-enhanced fluorescence is ideally suited in this regard, in that low quantum yield fluorophores are more favorable, the fluorescence enhancement factor in the presence of silver nanostructures given by $1/Q_0$ where $Q_0$ is the free-space quantum yield in the absence of metal. Subsequently MEF when applied to immunoassays, yields ultra bright assays, with a much higher Signal:Noise as compared to identical assays not employing the MEF phenomenon.

Preparation of Metal Islands

The island particles are prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Alternative procedures for preparing metal particles are also available. Silver is primarily used because of the familiar color from the longer surface plasmon absorption of silver.

Preparation of Silver Colloids

Colloids can be prepared as suspensions by citrate reduction metals. Preferred metals are silver and gold. Again, gold may be because of the absorption of gold at shorter wavelengths. However, gold colloids may be used with longer wavelength red and NIR fluorophores.

The size of the colloids and their homogeneity can be determined by the extensive publications on the optical properties of metal particles available and the effects of interface chemistry on the optical property of colloids.

Silver island films can be formed by a chemical reduction of a silver salt on the quartz surface, which are relatively simple to fabricate. However, this approach does not provide a control of particle size, or distance of the fluorophores from the surface. Enhancements of 1000 fold have been with the realization that sample geometries have been heterogeneous and the enhancement factors spatially averaged.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.

Positioning of the biomolecule or metal particle at a desired distance can be achieved by using a film. The film may be a polymer film, a Langmuir-Blodgett film or an oxide film.

Langmuir-Blodgett Films

Metal-fluorophore distances may be achieved by using Langmuir-Blodgett films with fatty acid spacers. The fatty acids may be from natural sources, including concentrated cuts or fractionations, or synthetic alkyl carboxylic acids. Examples of the fatty acids include, but not limited to, caprylic ($C_8$), capric ($C_{10}$), lauric ($C_{12}$), myristic ($C_{14}$), palmitic ($C_{16}$), stearic ($C_{18}$), oleic ($C_{18}$), linoleic ($C_{18}$), linolenic ($C_{18}$), ricinoleic ($C_{18}$) arachidic ($C_{20}$), gadeolic ($C_{20}$), behenic (C22) and erucic ($C_{22}$). The fatty acids with even numbered carbon chain lengths are given as illustrative though the odd numbered fatty acids can also be used.

Metal-fluorophore distances may be achieved by using polymer films. Examples of the polymer include, but not limited to, polyvinyl alcohol (PVA). Absorbance measurements and ellipsometry may be used to determine polymer film thickness. One type of polymer films is spin coated polymer film. The technology of spin coated polymer spacer films readily allows films to be coated onto a variety of surfaces, with varied thickness from >0.1 um. The coating can be performed on a spin coater, which allows uniform surface thickness by varying polymer concentration (viscosity) and spin speed. For example, Model P6700 spin coater (Specialty Coating Systems Inc.), allows uniform surface thickness by varying polymer concentration (viscosity) and spin speed.

In one embodiment, detection occurs without binding the molecules to the sensor or support. The molecule to be detected is not chemically bound. The molecule to be detected may remain in solution and not directly or indirectly interact with the metal particles, coatings or film spacer layers.

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

Polymers containing metal particles may have other applications, including but not limited to, size inclusion/exclusion sensing of non-fluorescent species, increased photostability of embedded fluorophores, single pore single molecule detection, and porous polymers which allow diffusing analytes or antibodies, resulting in a detectable and quantifiable signal change in the analyte or antibody or respective transduction element.

This embodiment of the present invention may also have vast applications in clinical medicine, environmental monitoring applications, homeland security such as rapid detection of low concentration species, industrial processes, pharmaceutical industries such as monitoring species, and sensors for use in reduced atmospheres such as biohazard clean rooms and space light.

Experimental Section

Materials. Fluorescein isothiocyanate-labeled human serum albumin (FITC-HSA), biotinamidocaproyl-labeled bovine serum albumin (biotinylated-BSA), FITC-labeled avidin, Rhodamine B-labeled avidin and Silane-Prep™ glass microscope slides (were purchased from Sigma-Aldrich Chemical Company (Milwaukee, Wis., USA).

Methods. Silver Island Films (SIFs). SIFs were prepared according to the previously published procedure.[11]

Characterization of SIFs before and after sonication using Absorption Spectroscopy. The absorption spectrum of SIFs (500 ul deionized water was placed onto SIFs before sonication) was measured before and after sonication (commercially available ultrasonic bath (Branson Ultrasonic Bath, Model no. B200, Input and Output power=25 and 19 W, respectively at 40 kHz; Irradiating surface area≈23 $cm^2$) up to 30 minutes (cumulative time) using a Varian Cary 50 Bio UV-vis spectrophotometer. The SIFs and glass slides were placed directly at the bottom of the ultrasonic bath without water.

Fluorescence Spectroscopy. An 10 uM aqueous solution of FITC-HSA was incubated on SIFs for 30 min followed by subsequent wash to remove unbound material. Fluorescence emission spectrum of FITC-HSA deposited onto SIFs were measured before and after sonication up to 20 minutes (cumulative time) using a Cary Eclipse fluorometer (500 ul deionized water was placed onto SIFs before sonication).

Atomic Force Microscope (AFM) Measurements, AFM images of SIFs before and after 1 min of sonication were taken using a Molecular Imaging Picoplus at a scan rate of 1 Hz with 512×512 pixel resolution in tapping mode.

SAMEF-based Model Bioassay. The model bioassay is based on the biorecognition event take place between biotin and avidin molecules. In the SAMEF-based assay, biotin groups were introduced to the SIFs and glass surfaces by a 30 minutes incubation of 10 uM aqueous solution of biotinylated-BSA on SIFs. It is well known that albumin is known to bind to silvered surface and indeed forms a monolayer.[19, 20] Unbound material was removed by multiple washes with deionized water. The biotinylated-BSA-coated SIFs and glass surface were placed inside the ultrasonic bath (without any liquid). SAMEF-based assay was carried out by incubating a 500 ul aqueous solution of the binding partner of biotin, FITC-labeled avidin, for 1 min under continuous sonication (the lid of the ultrasonic bath was closed). After the sonication was turned off, unbound material was removed by multiple washes with deionized water. Fluorescence spectrum of FITC-avidin on SIFs and glass surfaces was measured using a Cary Eclipse fluorometer. Control experiments, where the identical assay is run at room temperature without sonication, were also carried out for 30 min to validate the end-point results for SAMEF-based assays. Additional control experiments, where one of the binding partners (biotin) is omitted from the surfaces, were carried out as described above.

Fluorescence Resonance Energy Transfer (FRET) Studies. To investigate whether the sonication denatures protein is SAMEF-based assays, FRET studies were undertaken. In this regard, after the introduction of biotin groups as described in the previous section, two different avidin molecules labeled with a donor fluorophore (FITC) and an acceptor fluorophore (Rhodamine B) was incubated on the SIFs surfaces at room temperature for 30 min and in a separate experiments for 1 min under continuous sonication. In two separate experiments, the molar ratio of donor to acceptor was adjusted to 5:1 and 1:5. Fluorescence spectrum from these two different surfaces and two experiments were compared qualitatively for the extent of FRET between the donor and acceptor molecules.

Real-Time Thermal Imaging of SIFs and Glass Surfaces during Sonication. Real-time monitoring of temperature changes on SIFs and glass surfaces were measured using a commercially available thermal imaging camera (Silver 420M; Electrophysics Corp, Fairfield, N.J., equipped with a close-up lens that provides a resolution of approximately 300 um). In this regard, 500 ul of deionized water was placed on SIFs and glass surfaces placed inside the ultrasonic bath. Temperature of the water on the both surfaces (in separate experiments) was measured for 2 min, including a 1 min sonication period.

Results and Discussion

For low-intensity ultrasound to be used in MEF applications, it is pertinent to study the effect of sonication on the physical properties of the SIFs. In this regard, optical absorption spectroscopy, atomic force microscopy and fluorescence spectroscopy techniques were employed. FIG. 1A shows the absorption spectrum of SIFs before and after the sonication for a total time 30 min. While no shift in the wavelength of the surface plasmon resonance (SPR) for silver nanostructures (≈420 nm) was observed, a slight broadening in the absorption spectrum at longer wavelengths (>550 nm) was evident. This implied that, after 1 min of sonication, the loss of silver nanoparticles from the glass surface was negligible and no change in the shape of the nanoparticles occurred. To verify the results of absorption spectroscopy studies, AFM images of SIFs were taken before and after 1 min sonication, c.f. FIGS. 1B and 1C. AFM images show that SIFs retained their shape and height. AFM images also show the number of nanoparticles is decreased after the sonication process (FIG. 1C). Due to the heterogeneous nature of SIFs and the difficulties in imaging the same location on SIFs before the sonication with AFM, these results were deemed inconclusive with regard to the loss of nanoparticles from the glass surface as a result of 1 min sonication.

Figure 2A:
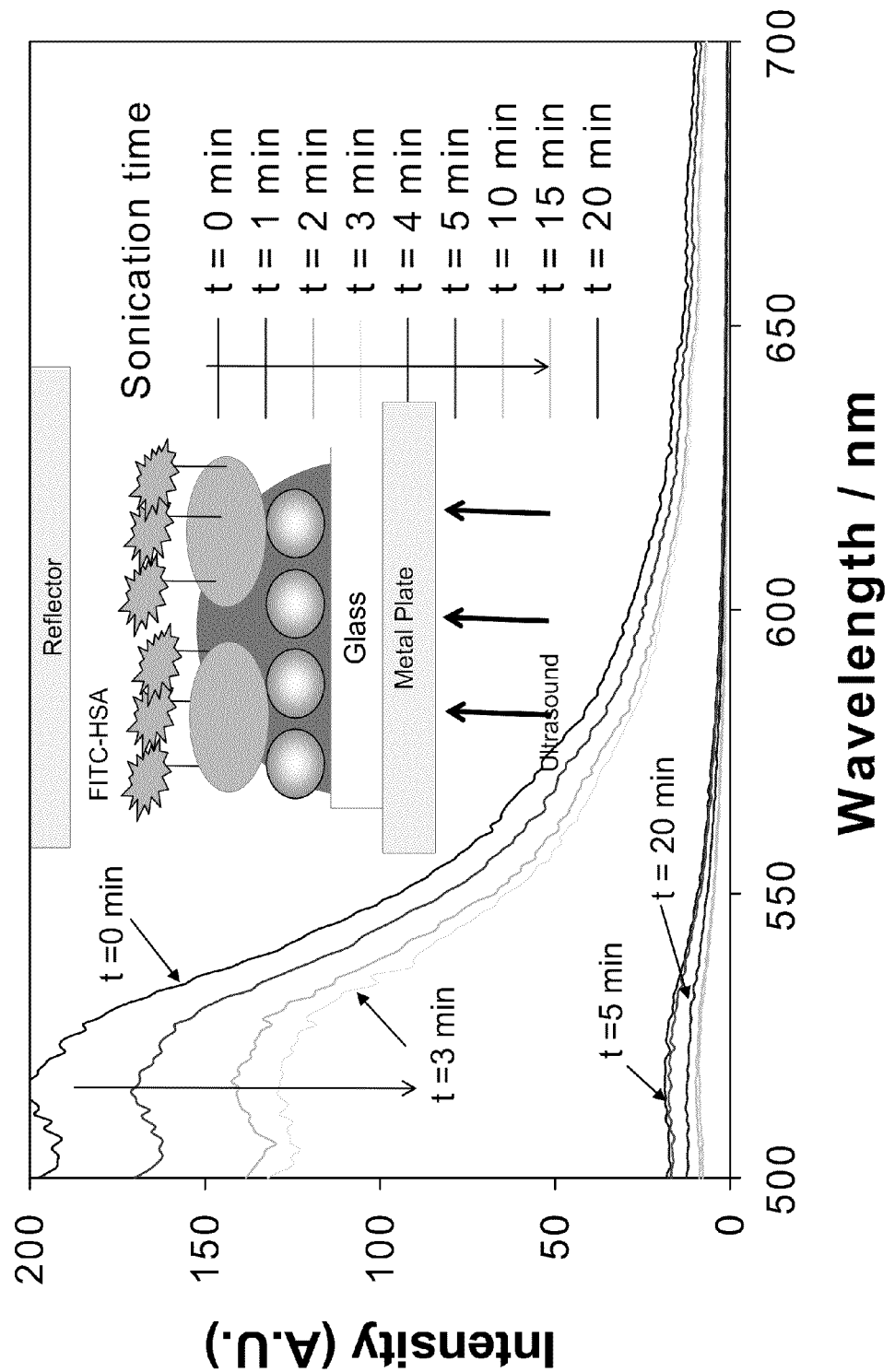
FIG. 2 (A) Fluorescence emission spectrum of FITC-HSA coated onto SIFs as a function of sonication time, (B) Real-color photograph of FITC-HSA coated SIFs before and after 20 minutes of sonication (these samples were dried with a stream of air). In all these experiments 500 microliter of deionized water was placed on top of the samples (white dashed circles). The reflector plate is located 2 cm from the surface of the glass.
Figure 2B:
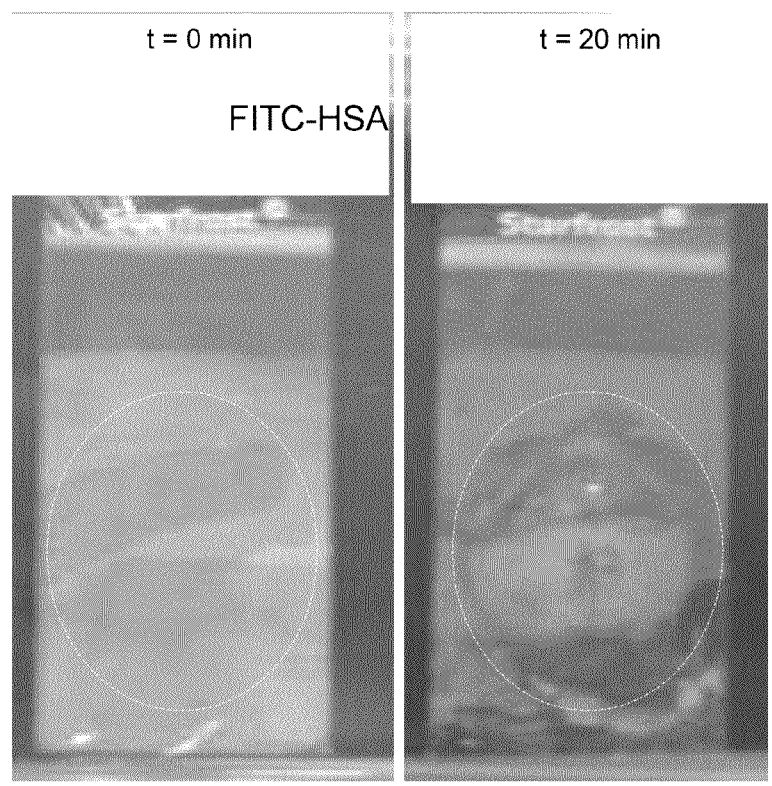
Figure 3A:
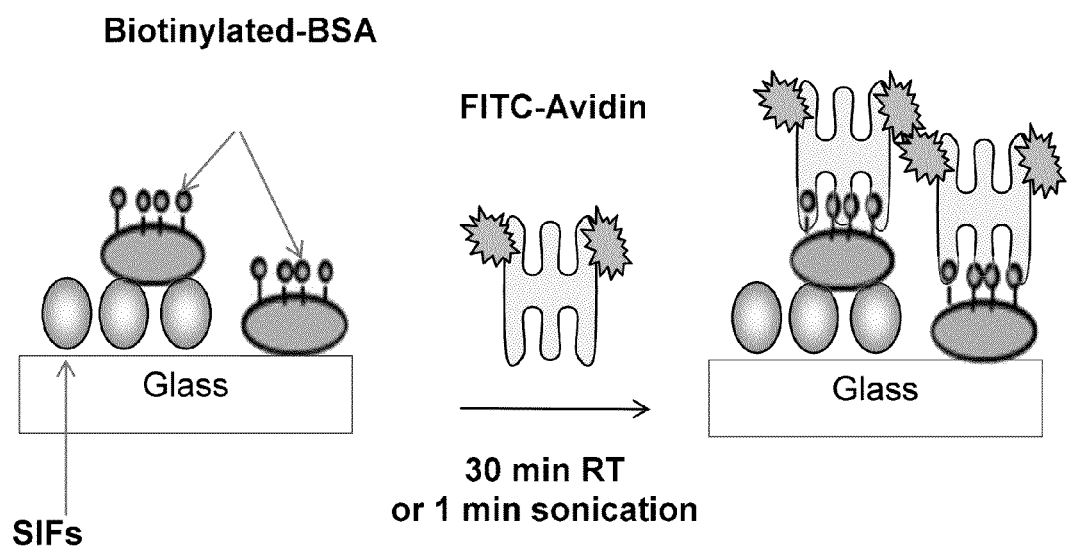
FIG. 3 (A) Experimental scheme for a model protein assay run at room temperature (RT) or with sonication, (B) Cartoon depiction of Metal-Enhanced Fluorescence phenomenon and real-color photographs of fluorescence emission from SIFs and glass visually demonstrating the utility of MEF, (C) Fluorescence emission spectrum of FITC-Avidin used in the model protein assay run on SIFs and glass at RT and with sonication, Inset—Real-color photograph of SIFs after the model protein assay is run with sonication, SIFs appear to be not destroyed as a result of 1 min sonication, (D) Control experiment, where biotinylated BSA (B-BSA) is omitted from the surfaces, corresponding to model assays run on SIFs (1) and on glass (3), shown in (B).
Figure 3B:
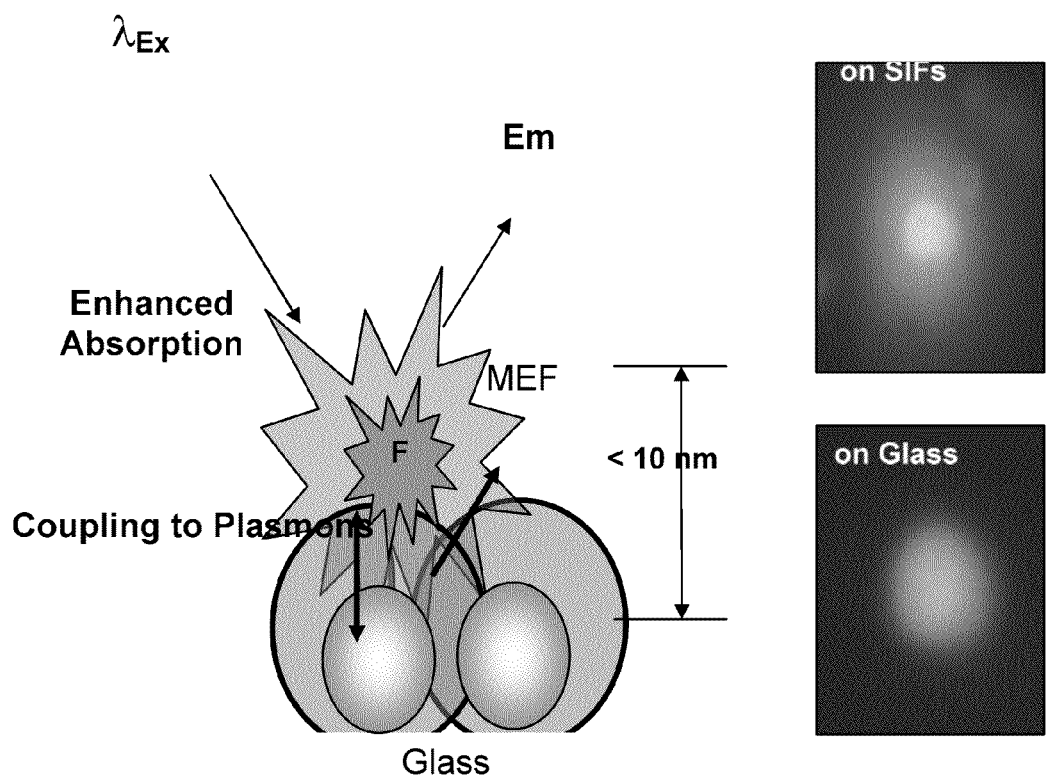
Figure 3C:
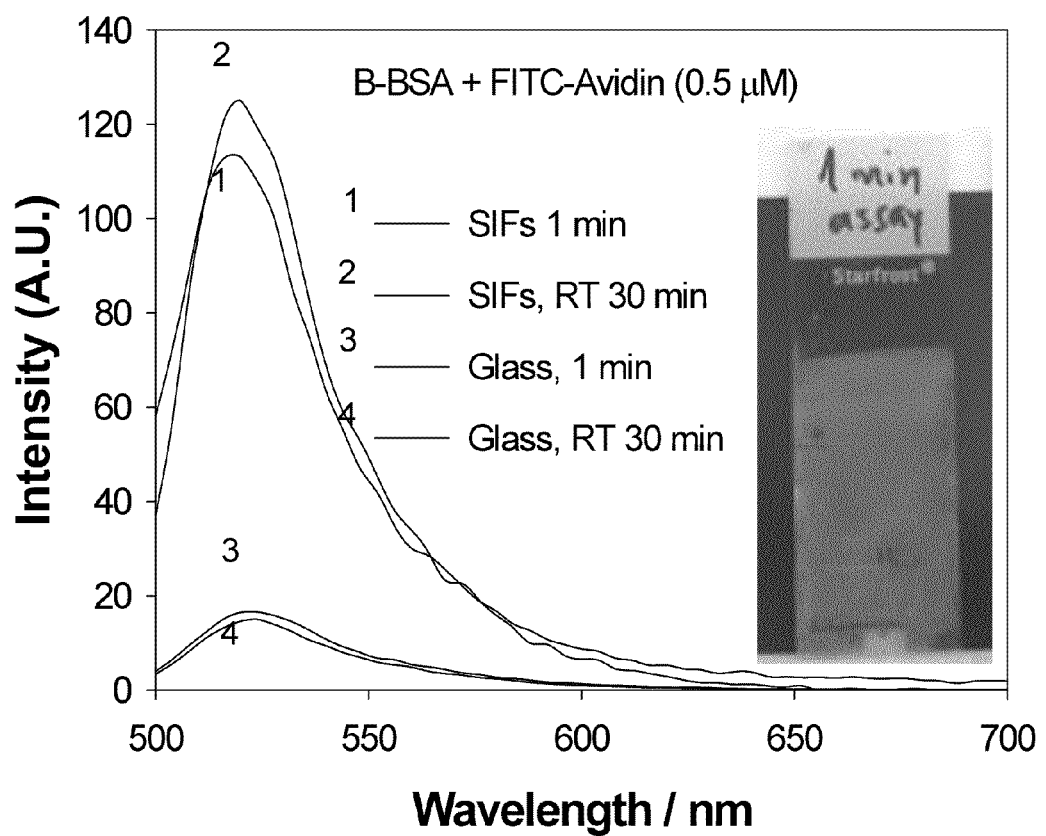
Figure 3D:
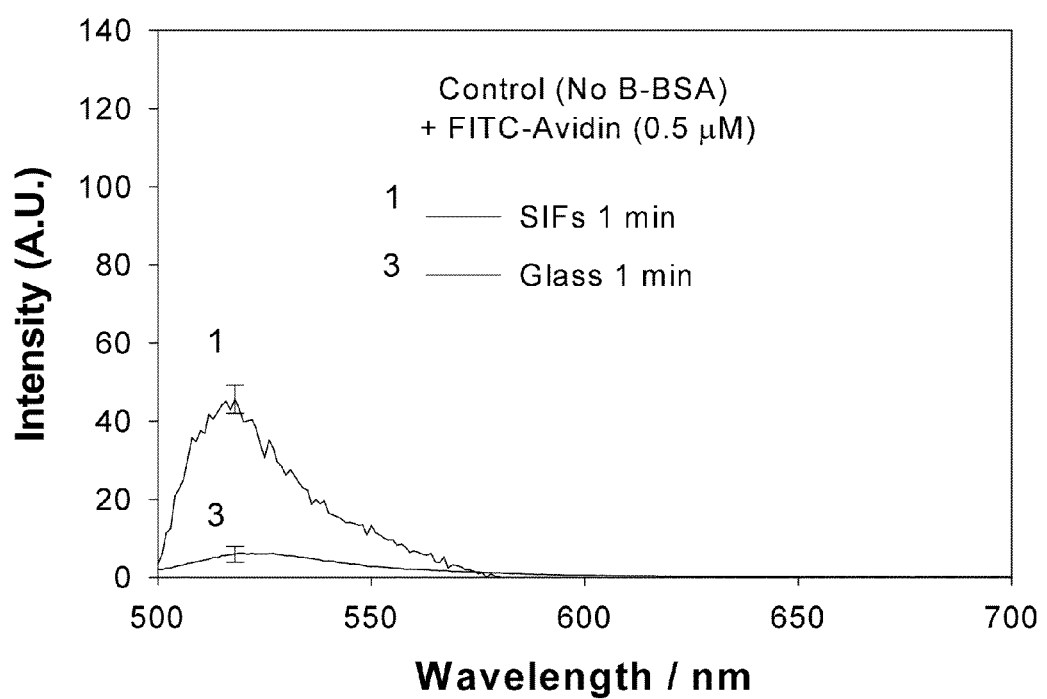
Figure 4A:
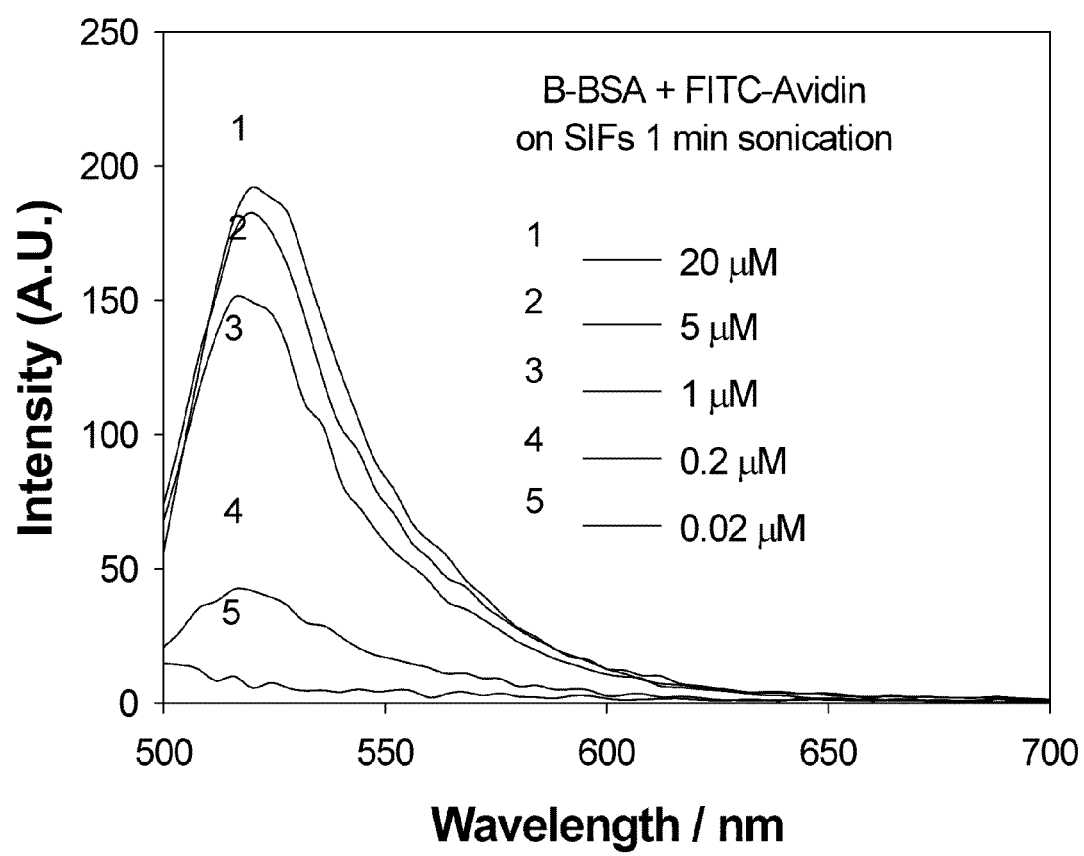
FIG. 4 (A) Fluorescence emission spectrum of FITC-Avidin used in the model protein assay run on SIFs, and glass (C) with sonication (1 minute) Identical model protein assay run on SIFs (B) and on glass (D) at room temp.
Figure 4B:
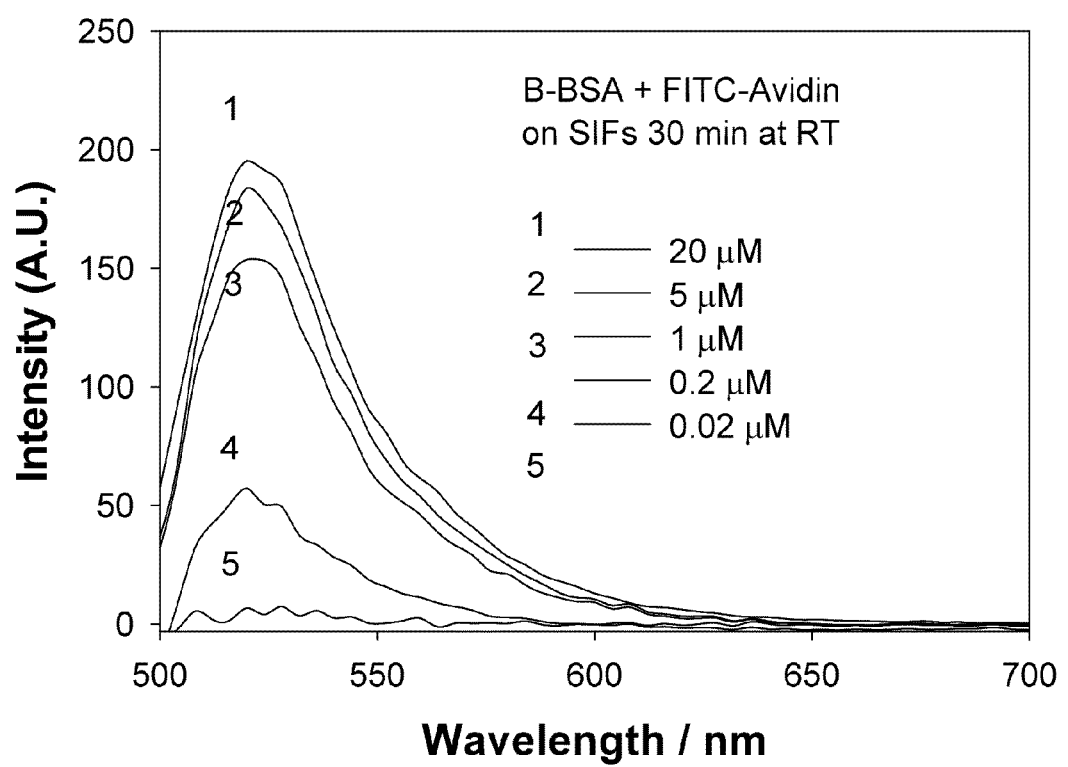
Figure 4C:
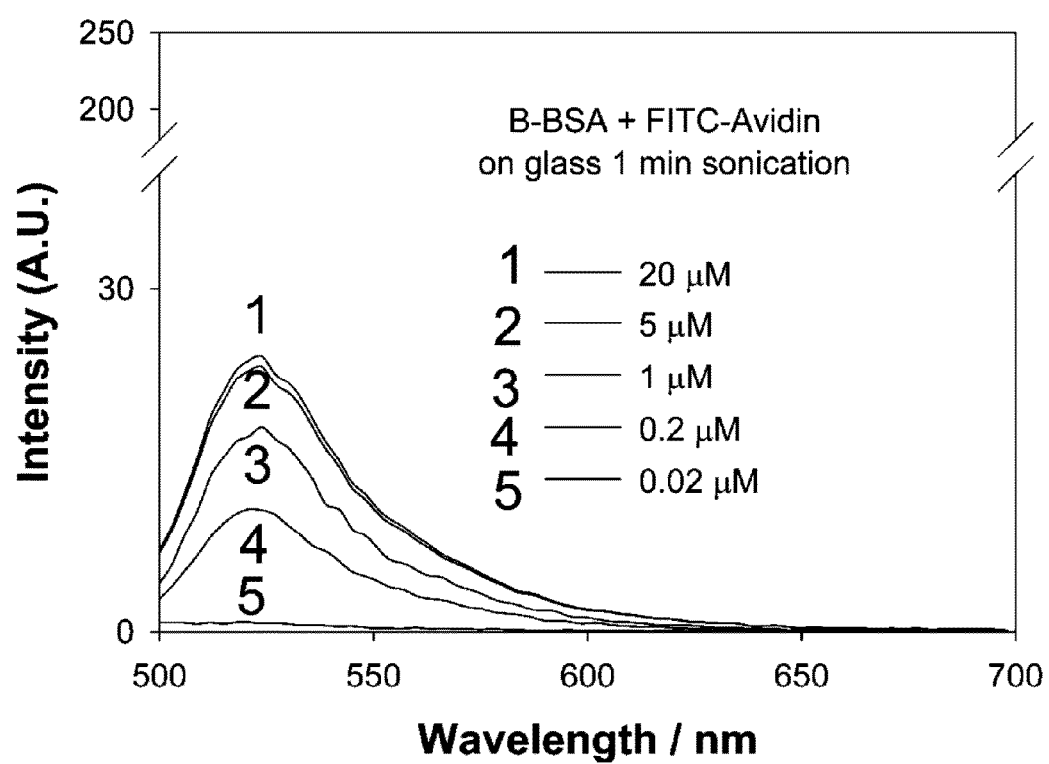
Figure 4D:
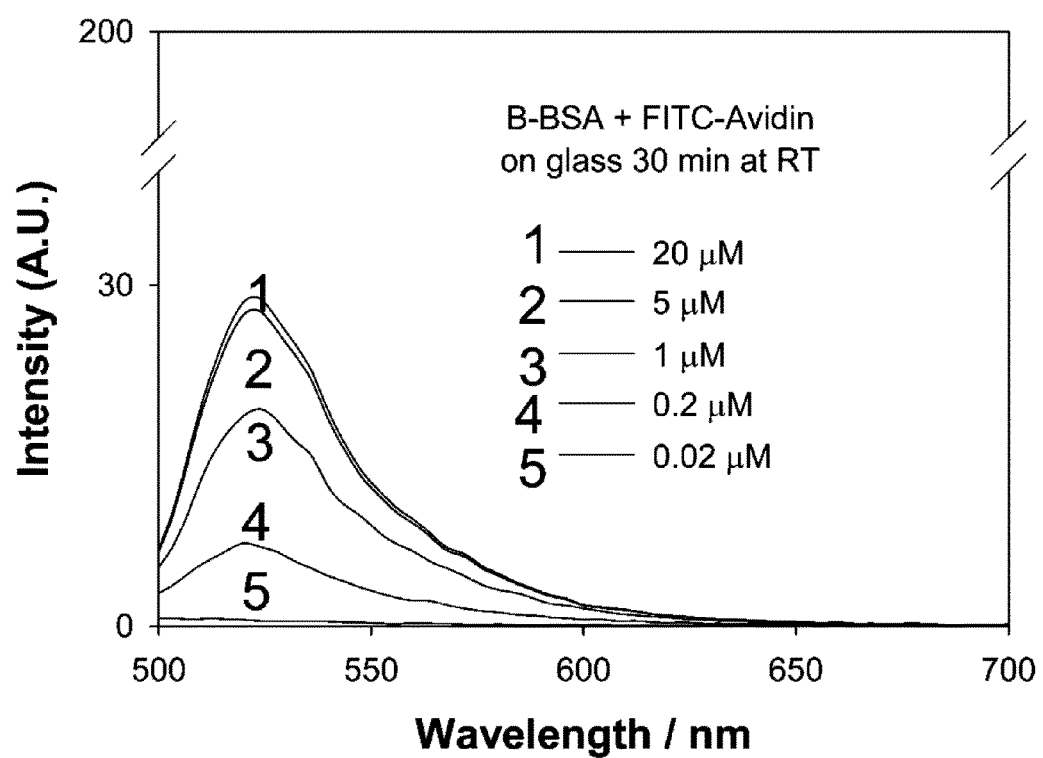

Since the SAMEF-based bioassays involve the interactions of biological materials on SIFs and the subsequent detection of fluorescence emission from the surface, it is also important to study the effect of sonication on SIFs and MEF phenomenon. FIG. 2A shows the fluorescence emission spectrum of FITC-HSA coated onto SIFs as a function of sonication time. The fluorescence emission from FITC show a ≈15% reduction after 1 min sonication, which increases to ≈40% after 3 min. No detectable fluorescence emission was observed after only 4 min of sonication, which implies that FITC-HSA is removed from the surface. This can be due to either the removal of FITC-HSA molecules alone or the removal of FITC-HSA molecules with silver nanoparticles as a result of sonication. Visual evidence for the removal of FITC-HSA/SIFs was provided with the real-color photographs of FITC-HSA coated SIFs before and after 20 min sonication, FIG. 2B, which show a significant removal of SIFs from the surface. Based on the observations described above it was concluded that the longest period of time of sonication while retaining all components of the SAMEF-based bioassays their functions is from about 30 sec. to 90 sec minutes and more preferably about 60 seconds.

FIG. 3 summarizes the experimental design and the proof-of-concept of SAMEF-based bioassays based on the interactions of biotin and avidin, a model assay. In this regard, biotinylated-BSA is attached to SIFs and glass surfaces, c.f. FIG. 3A. Subsequently, fluorophore (FITC)-labeled avidin is incubated on these surfaces for 1 min with sonication or for 30 min at room temperature without sonication. Fluorescence emission from FITC-avidin is measured from both SIFs and glass to show the benefits of MEF. Since SAMEF technique also is based MEF phenomenon, it is important to briefly discuss MEF. In MEF (FIG. 3B), an increased fluorescence emission from fluorophore/SIFs "system" as compared to glass surfaces is typically observed. This is attributed to the partial energy transfer (coupling to surface plasmons) between the fluorophores and the surface plasmons and to enhanced absorption of light by the fluorophores as a result of increased electric fields near nanoparticles.[21] FIG. 3C shows the fluorescence emission from the model assay run on SIFs and glass surfaces with sonication for 1 min and at room temperature without sonication for 30 min (a control assay). The emission intensity at 520 nm from the control assay serves as target emission intensity for assays run with sonication to verify that sonicated assays indeed goes to same end point as assay run at room temperature. FIG. 3C shows that the model assay both run on SIFs and glass surfaces reached to >95% completion in 1 min when compared to room temperature assay. The emission intensity at 520 nm for the model assay was ≈6-fold larger on SIFs than glass demonstrating the benefits of using silver nanoparticles in the surface assays. To determine the extent of non-specific binding of FITC-avidin to surfaces in assays run with sonication, additional control experiments where biotinylated-BSA is omitted from the surfaces are undertaken, c.f. FIG. 3D. The non-specific binding was found to be $\frac{1}{3}^{rd}$ that of the assay run both on SIFs and glass surfaces. It is important to note that no additional surface chemistries were employed to reduce the non-specific binding in this study, that is, only the biological binding partners were present on the surface. One can reduce the non-specific binding by blocking the surfaces of silver nanoparticles with self-assembled monolayers of polyethylene glycol modified alkanethiols that resist the non-specific binding of proteins.[22]

Figure 5:
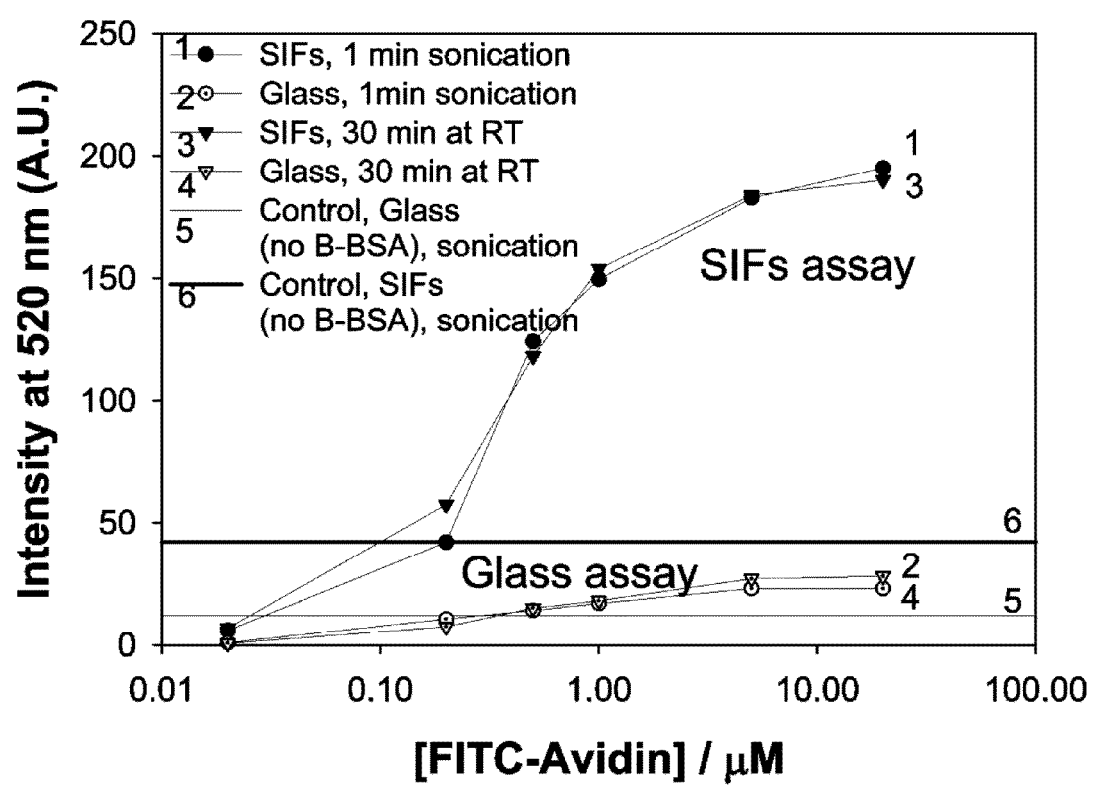
FIG. 5 Fluorescence emission intensity (at 520 nm) versus concentration of FITC-Avidin used in the model protein assay run on SIFs and glass at room temperature and with sonication (1 minute).

Next, the dynamic range of concentration of FITC-avidin using SAMEF-based technique was determined and the results with the model assay run without sonication compared as shown in FIGS. 4 and 5. FIGS. 4 A to D show that fluorescence emission from FITC-avidin increases as the concentration increases for the assays run using sonication and without sonication, respectively. FIG. 5 shows that the end-point values for emission intensities at 520 nm from assays run both on SIFs and glass surfaces with and without sonication are identical, proving the successful employment of sonication in MEF assays. FIG. 5 also shows the lower-detection limit of >0.2 uM for assays both run on SIFs and glass surfaces with sonication, when the control experiments run using the largest concentration of FITC-avidin in the absence of biotinylated-BSA are considered. The benefits of using silver nanoparticles, increased intensities over the dynamic range of concentration for FITC-avidin as compared to glass, in the assay are also evident from FIG. 5.

Figure 6A:
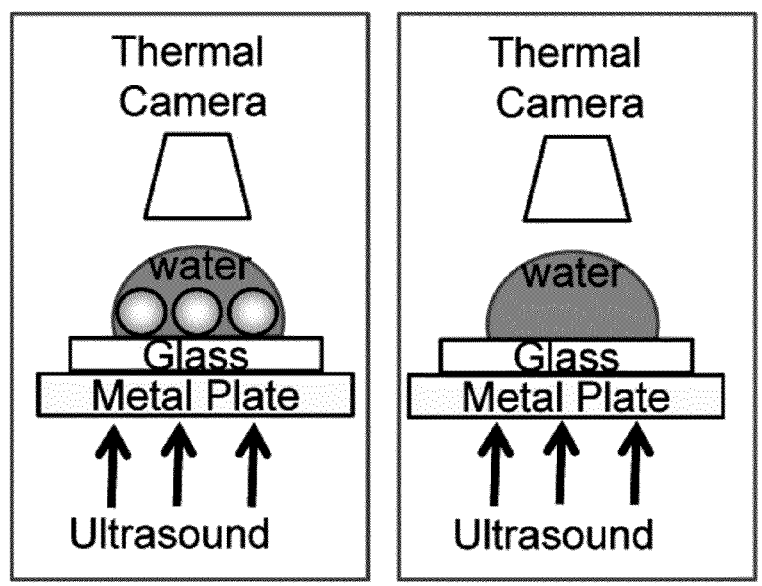
FIG. 6 (A) Experimental scheme for real-time temperature imaging of SIFs and glass before, during and after sonication (total sonication time: 1 minute), (B) Thermal images of SIFs and glass before and after 1 minute sonication. The location of the glass slides are indicated by solid lines (white and black). Average temperature values of water are measured from a region shown with dashed white circles in the middle of the glass slides (C) Real-time temperature of water on SIFs and glass before, during and after sonication (1 minute). The sonication was turned on and off at t=5 and 65 seconds, respectively.
Figure 6B:
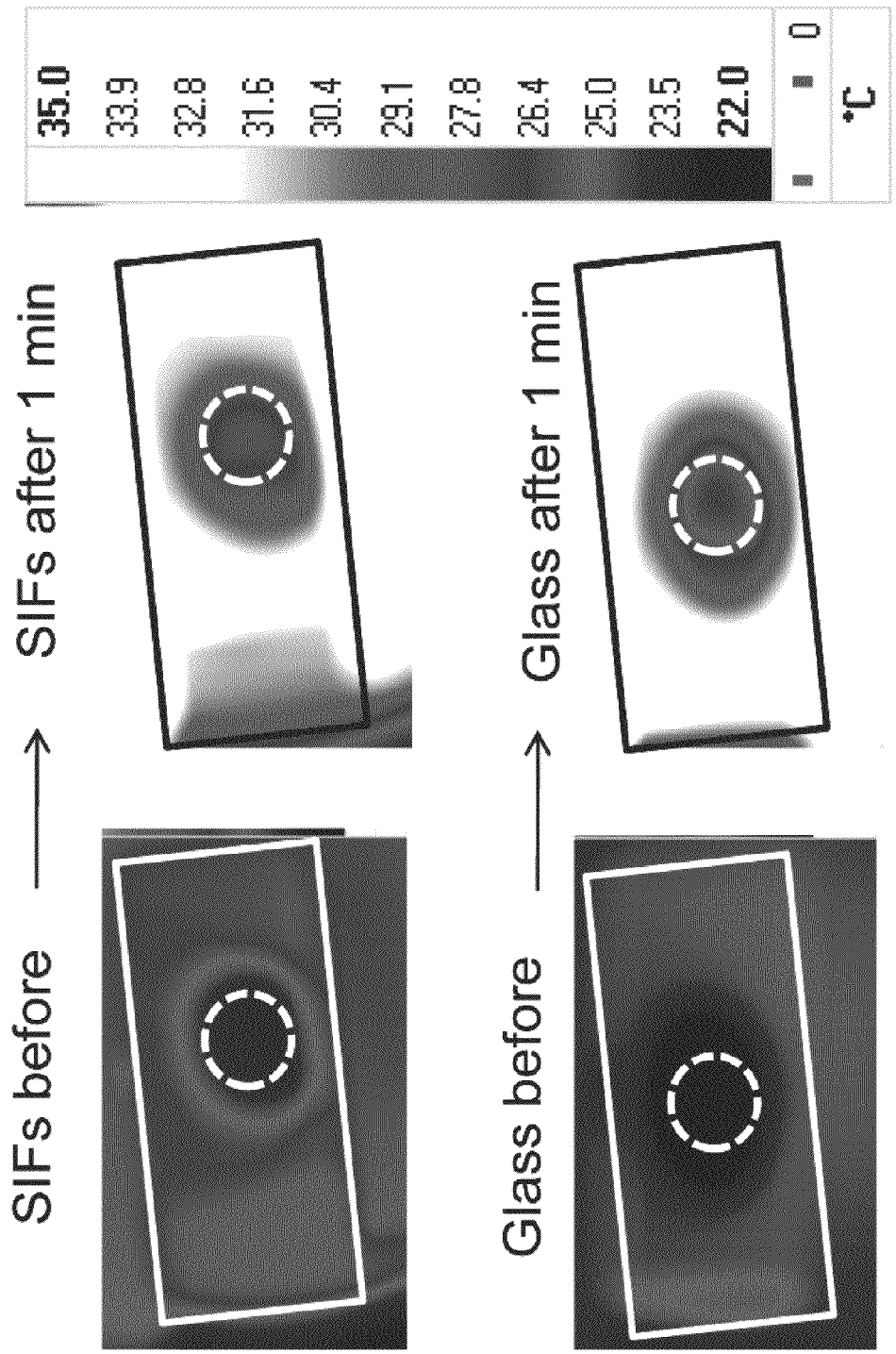
Figure 6C:
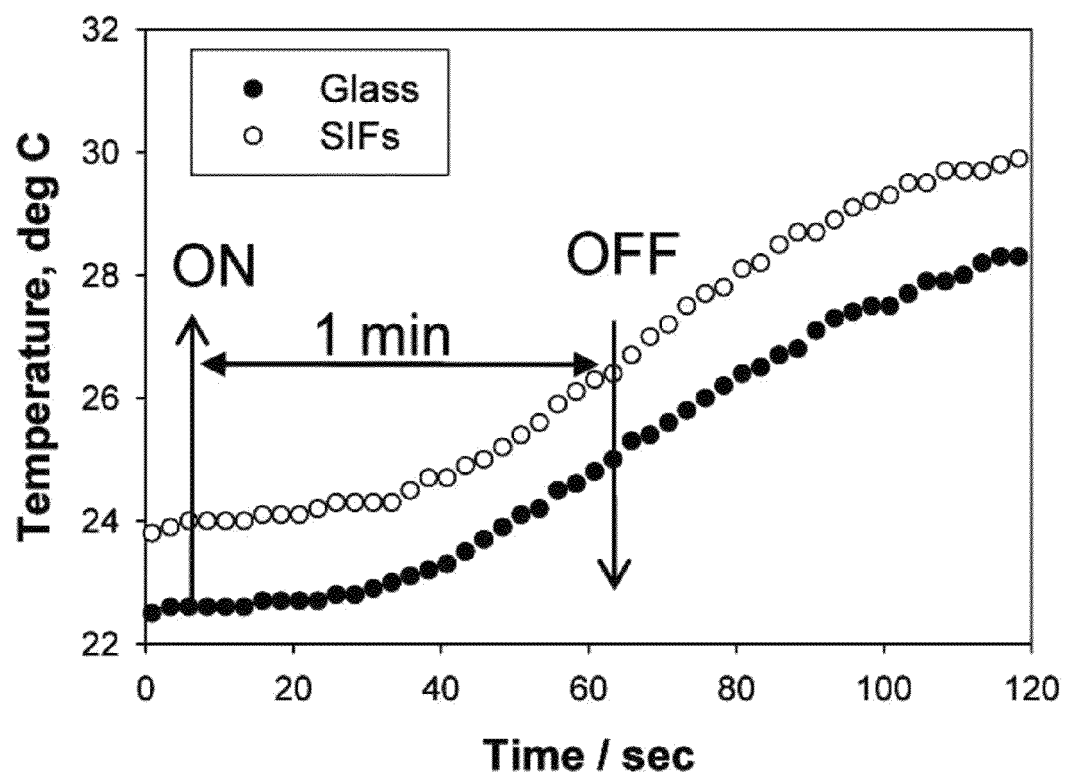

An increase in the temperature of the SIFs and glass surfaces was observed during the collection of data presented in FIGS. 1-3. To determine the extent of increase in temperature of water, real-time imaging of the temperature of the assays on SIFs and glass surfaces were recorded using a thermal camera. FIG. 6A shows the experimental geometry for the real-time temperature measurements. The experimental geometry was kept identical to that of the assays for the sake of consistency. In this experimental geometry, SIFs and glass substrates were placed at the bottom of an ultrasonic bath (in separate experiments), where the thermal image of water and SIFs/glass surfaces were captured for 2 minutes including a 1 minute of sonication. FIG. 6B shows the thermal images for SIFs and glass surfaces before and after 1 min of sonication. Average temperature of water placed on these surfaces show a $\approx 2°$ C. increase on both SIFs and glass surfaces, while the temperature of regions of SIFs and glass surfaces not covered with water (dry, assays are not constructed on these regions) increase by up to $\approx 13°$ C. This contributes to the further increase (additional $\approx 3°$ C.) in temperature of water due to heat transfer even after the sonication is turned off as shown in FIG. 6C. It is important to note that the assay (FIGS. 3 and 4) was stopped and the unbound material was washed off immediately after the sonication was turned off after 1 min.

Figure 7A:
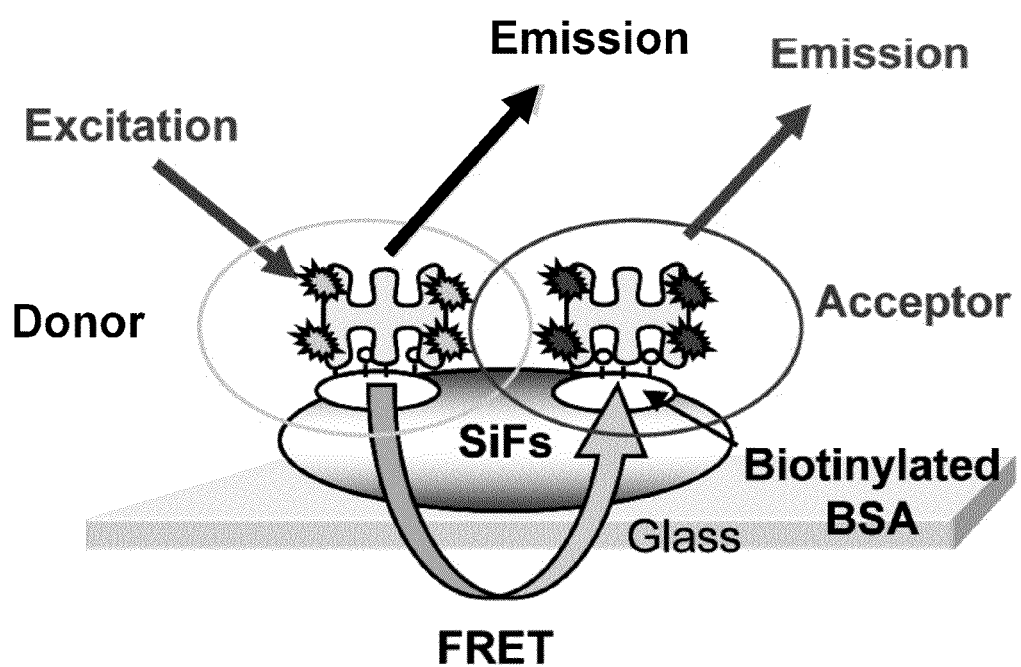
FIG. 7 Fluorescence Resonance Energy Transfer studies performed on SIFs. Donor (FITC) and acceptor (Rhodamine B) molecules are bound to separate avidin molecules, which subsequently bind to biotinylated BSA on the surface of SIFs as shown in FIG. 7A. The molar ratio of donor to acceptor molecules was (B) 5:1, (C) 1:5.
Figure 7B:
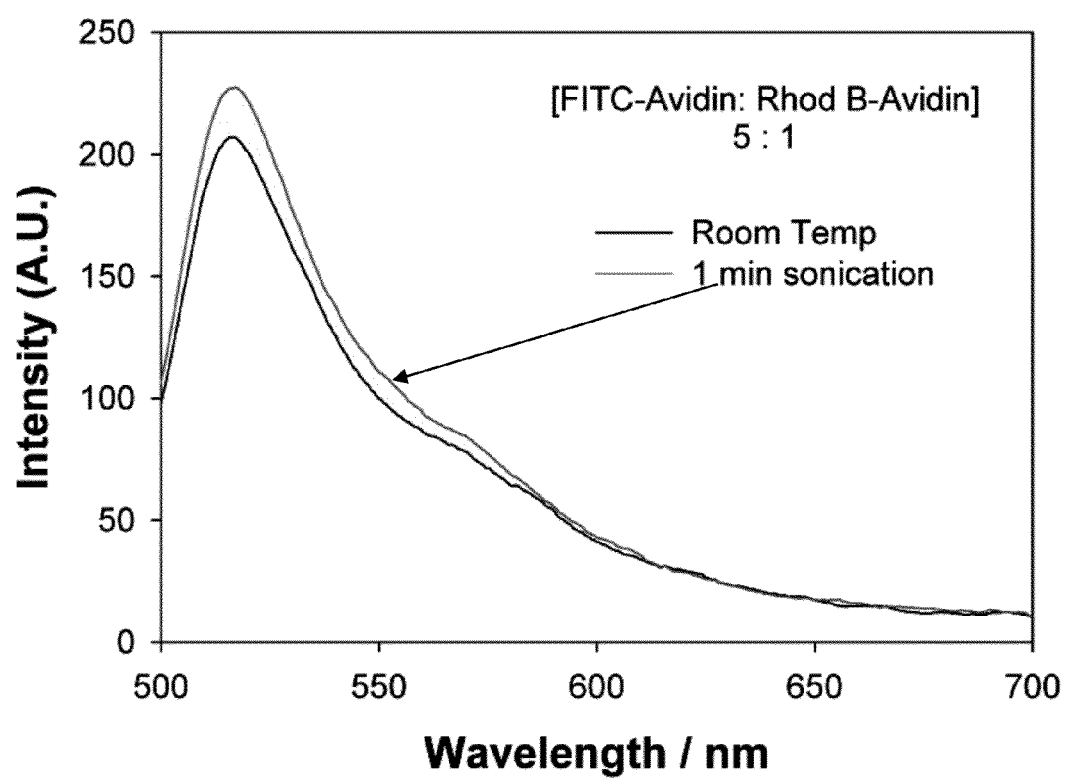
Figure 7C:
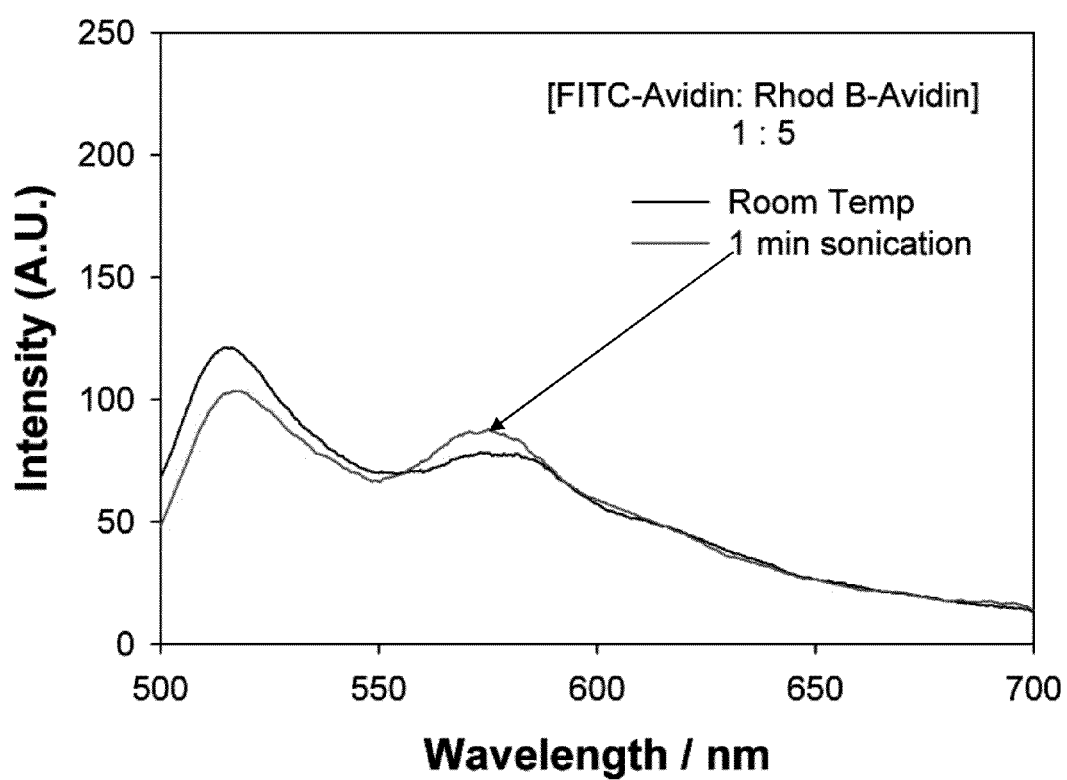
Figure 8:
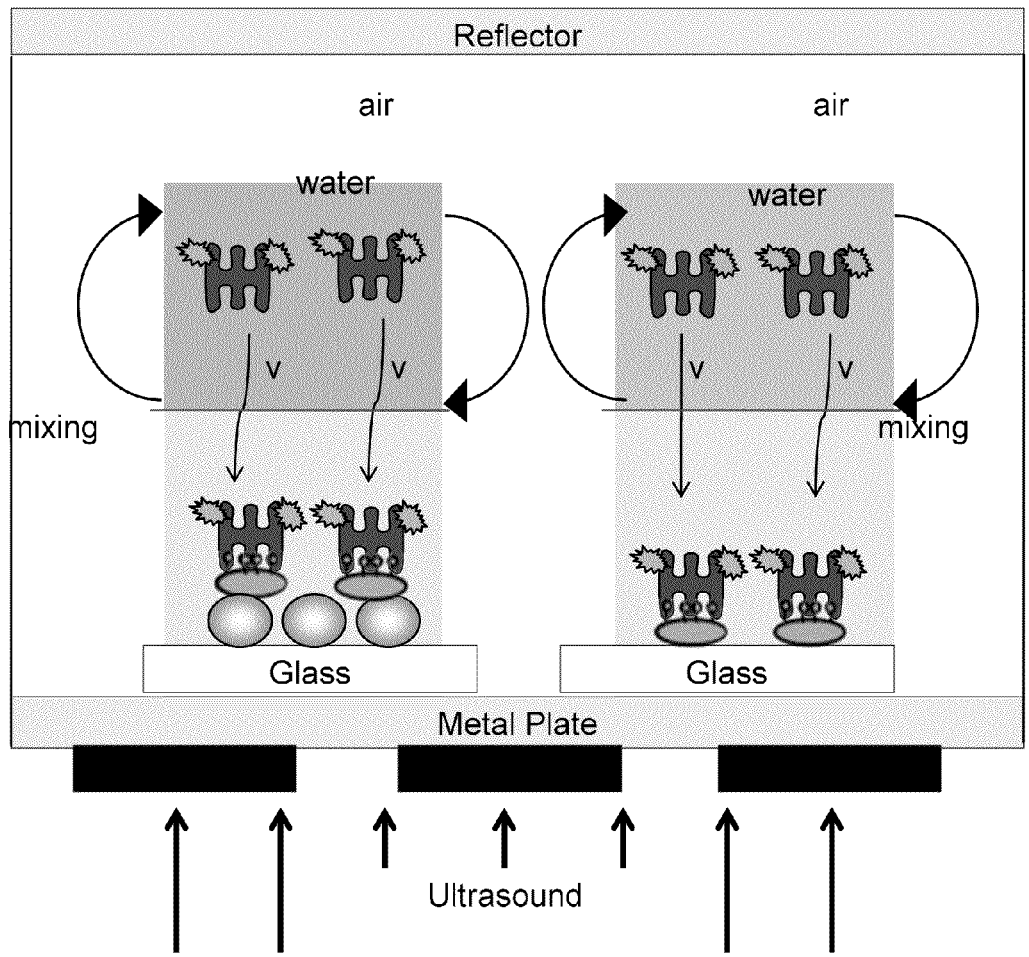
FIG. 8 shows movement and mixing of biomolecules to the binding substrate.

It was thought that the combination of sonication and increase in temperature can result in protein denaturation and/or conformational changes on the assay surface and adversely affect the sensitivity of the assay that is based on MEF. Since MEF is a distance-dependent phenomenon any conformational changes in proteins due to sonication and increase in temperature can yield results not comparable to assays run using conventional methods, and thus can deem SAMEF-based assays unusable. In this regard, FRET, a technique widely used in the studies of protein conformational changes, is employed to investigate the effect of sonication and increase in temperature on the assay components. In the FRET experiments, donor (FITC) and acceptor (Rhodamine B) molecules bound to different avidin molecules were incubated on biotinylated BSA-coated surfaces together with (1 min) and without sonication (control experiment run at room temperature for 30 min) as shown in FIG. 7A. FIG. 7B shows the results of these FRET experiments for two different molar ratios of donor to acceptor (5:1 and 1:5). For a ratio of 5:1, the emission spectrum is dominated by FITC emission (primarily because it is excess) and the emission spectra are identical for assays run both with and without sonication, suggesting that biotinylated-BSA and avidin have not undergone conformational changes and these assay reached the same end-point in 1 and 30 min with and without sonication, respectively. Further evidence for this was also observed when the donor to acceptor molecule ratio was 1:5 and is shown in FIG. 7C. The emission is no longer dominated by donor emission but instead significant FRET was observed to the acceptor. These results also imply that the absorption of ultrasound by proteins did not affect their ability to bind other proteins.

Since the SAMEF-based assays are based on the combined use of low intensity ultrasound, MEF and surfaces, it is important to discuss the possible explanations for the observation of quicker assay times with the employment of sonication. Ultrasound (at 40 kHz) is used to remove materials from surfaces, usually in water (with the help of surfactants) due to cavitation effects. Cavitation is produced by introducing ultrasound waves into a liquid and is referred to as rapid formation and implosion of small bubbles in a liquid.[15] The implosion of bubbles result in hot spots in liquids and the temperature inside the bubble can reach in excess of 5000K, which is subsequently quenched by surrounding water molecules at a rate of $10^{10}$ K/sec.[15] At 40 kHz, the ultrasound waves form far away (a few micrometers) from the surface and this distance decreases as the frequency of the ultrasound waves increases, which implies that ultrasound waves do not interact with nanoscale particles on a planar surface. When cavitation occurs in a liquid near a solid surface (like glass slides in this study), the implosion of bubbles result in jets of liquid that move towards the solid surface at high speeds.[18] This movement of liquid can result in transfer of proteins in the bulk solution towards the surfaces, which decreases the amount of proteins in the bulk of the solution. In addition, ultrasound waves form a standing wave in the bulk of assay medium,[15] which provides a means of movement of proteins, effectively mixing the assay components in the bulk solution. Subsequently, proteins are thought to continuously move towards the surface for the duration of the sonication (1 min) while longer sonication times resulted in the removal of assay components from the surface. Thus, the observation of quicker assays times using low-intensity ultrasound is attributed to the increased mass transfer of proteins as a result of the interaction of ultrasound with assay components.

Conclusions

A new bioassay technique, called Sonication-Assisted Metal-Enhanced Fluorescence, which is based on the combined use of ultrasound waves and silver nanoparticles to accelerate bioassay kinetics and enhance fluorescence signatures, respectively is reported. In this regard, a model bioassay, based on the interactions of biotin and fluorophore-labeled avidin, was constructed on SIFs and was subsequently completed in about 30 sec to 90 sec and preferably 60 seconds using ultrasound at 30 to 50 kHz, and preferably 40 kHz. Similar end-point values for fluorescence emission from sonicated assays were measured as those measured from assays carried out at room temperature without sonication, which confirms the accuracy of the new technique. The effect of sonication on the assay components were studied in detail using optical absorption spectroscopy, atomic force microscopy and fluorescence spectroscopy techniques. Optical absorption studies showed that continuous sonication of SIFs for about 60 seconds did not remove silver nanoparticles from the surface. In addition, a slight decrease in fluorescence emission from a fluorophore-labeled protein adsorbed onto SIFs after about 60 seconds of sonication was observed. AFM results showed the size and the shape of the silver nanoparticles did not undergo any changes, however these results were deemed inconclusive due to difficulty of imaging the same location on SIFs before the sonication with AFM. Thermal images of the assay show an ≈2° C. increase in temperature of the assay components after about 60 seconds sonication. The effect of sonication on protein denaturation or conformational changes was studied with FRET experiments, which showed that about 60 seconds sonication (and subsequent increase in temperature) did not result in protein conformational change.

REFERENCES

The contents of all references cited herein are incorporated by reference herein for all purposes.

(1) Collings, F. B.; Vaidya, V. S. *Toxicology* 2008, 245, 167-174.
(2) Lalvani, A.; Meroni, P. L.; Millington, K. A.; Modolo, M. L.; Plebani, M.; Tincani, A.; Villalta, D.; Doria, A.; Ghirardello, A. *Clin Exp Rheumatol* 2008, 26, S62-66.
(3) Taipa, M. A. *Comb Chem High Throughput Screen* 2008, 11, 325-335.
(4) Enander, K.; Choulier, L.; Olsson, A. L.; Yushchenko, D. A.; Kanmert, D.; Klymchenko, A. S.; Demchenko, A. P.; Mely, Y.; Altschuh, D. *Bioconjug Chem* 2008.
(5) Schultz, E.; Galland, R.; Du Bouetiez, D.; Flahaut, T.; Planat-Chretien, A.; Lesbre, F.; Hoang, A.; Volland, H.; Perraut, F. *Biosens Bioelectron* 2008, 23, 987-994.
(6) Matveeva, E.; Gryczynski, Z.; Gryczynski, I.; Malicka, J.; Lakowicz, J. R. *Analytical Chemistry* 2004, 76, 6287-6292.
(7) Matveeva, E.; Malicka, J.; Gryczynski, I.; Gryczynski, Z.; Lakowicz, J. R. *Biochem Biophys Res Commun* 2004, 313, 721-726.
(8) Aslan, K.; Gryczynski, I.; Malicka, J.; Matveeva, E.; Lakowicz, J. R.; Geddes, C. D. *Current Opinion in Biotechnology* 2005, 16, 55-62.
(9) Aslan, K.; Lakowicz, J. R.; Szmacinski, H.; Geddes, C. D. *Journal of Fluorescence* 2005, 15, 37-40.
(10) Geddes, C. D.; Lakowicz, J. R. *Journal of Fluorescence* 2002, 12, 121-129.
(11) Aslan, K.; Geddes, C. D. *Analytical Chemistry* 2005, 77, 8057-8067.
(12) Aslan, K.; Zhang, Y.; Hibbs, S.; Baillie, L.; Previte, M. J.; Geddes, C. D. *Analyst* 2007, 132, 1130-1138.
(13) Aslan, K.; Holley, P.; Geddes, C. D. *Journal of Immunological Methods* 2006, 312, 137-147.
(14) Thornycroft, L. H.; Barnaby, S. W. *Min. Proc. Inst. Chem. Eng,* 1895, 122 51-69.
(15) Suslick, K. S. *Science* 1990, 247, 1439-1445.
(16) Gould, R. K.; Coakley, W. T.; Grundy, M. A. *Ultrasonics* 1992, 30, 239-244.
(17) Suslick, K. S.; Flannigan, D. J. *Annu Rev Phys Chem* 2008, 59, 659-683.
(18) Neppiras, E. A. *Phys. Rep.* 1980, 61, 159-251.
(19) Aslan, K.; Geddes, C. D. *Journal of Fluorescence* 2006, 16, 3-8.
(20) Green, N. M.; Geddes, C. D., Protein Chem. 1975, 29, 85-133.
(21) Aslan, K., Leonenko, Z., Lakowicz. J. R., Geddes, C. D., J. Fluoresc. 2005, 15, 643-654.
(22) Lofas, S.; Malmqvist, M.; Ronnberg, I.; Stenberg, E.; Liedberg, B.; Lundstrom, I. *Sensors and Actuators B-Chemical* 1991, 5, 79-84.

That which is claimed is:

1. A method of decreasing detection time of a metal-enhanced fluorescence assay for detection of same target molecules in a sample, the method comprising:
    applying a multiplicity of metallic particles to a substrate surface, wherein the metallic particles are nanostructures, island or colloids, and wherein the substrate surface is glass, quartz or polymeric material;
    connecting capture molecules to the metallic particles, wherein the capture molecules have binding affinity for the target molecules;
    introducing a solution suspected of including the target molecules;
    applying sonic energy to the assay system for a time period sufficient to increase movement of the target molecules towards the metallic particles thereby binding with capture molecules, wherein the sonic energy is applied from 30 seconds to 90 seconds and is delivered at a range from 20 kHz to 60 kHz;
    introducing fluorescence detector molecules having affinity for the target molecules, wherein the fluorescence detector molecules can be added before, during or after the application of sonic energy and wherein the fluorescence detector molecules are positioned from about 5 nm to about 50 nm from the metallic particles;
    applying electromagnetic energy at a frequency to excite the fluorescence molecules; and
    measuring any fluorescence signal.

2. The method of claim 1, wherein the metallic particles comprise silver, gold, copper, zinc, nickel, iron, aluminum, palladium, or platinum.

3. The method of claim 1, wherein the metallic particles have a shape having at least one apex wherein the shape includes but is not limited to a triangle, square, rectangle, trapezoid, polygon, elliptical, oblong or combinations thereof.

4. The method of claim 1, wherein the fluorescence detector molecule comprises a biomolecule and wherein the biomolecule has affinity for the target molecules.

5. The method of claim 4, wherein the capture molecules, target molecules and fluorescence detector molecules comprise DNA sequences.

6. The method of claim 1, wherein the step of applying electromagnetic energy can be conducted before, during or after the applying of sonic energy.

* * * * *